US010307289B2

(12) United States Patent
Benner et al.

(10) Patent No.: US 10,307,289 B2
(45) Date of Patent: *Jun. 4, 2019

(54) SUB-CUTANEOUS MEDICINAL DOSAGE DELIVERY IMPLANT SYSTEM

(71) Applicant: DRUG DELIVERY COMPANY LLC, Salisbury, MD (US)

(72) Inventors: Jeffrey D. Benner, Salisbury, MD (US); Steven M. Cohen, St. Petersburg, FL (US); Christopher Forrest Lumpkin, Evergreen, CO (US)

(73) Assignee: Drug Delivery Company, LLC, Salisbury, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/662,822

(22) Filed: Jul. 28, 2017

(65) Prior Publication Data
US 2018/0049918 A1    Feb. 22, 2018

Related U.S. Application Data

(60) Provisional application No. 62/377,092, filed on Aug. 19, 2016.

(51) Int. Cl.
*A61F 9/007* (2006.01)
*A61M 29/02* (2006.01)
(52) U.S. Cl.
CPC ......... *A61F 9/00727* (2013.01); *A61M 29/02* (2013.01); *A61M 2210/0612* (2013.01)
(58) Field of Classification Search
CPC ... A61F 9/00727; A61F 9/0008; A61F 9/0017
See application file for complete search history.

(56) References Cited

U.S. PATENT DOCUMENTS 4,686,962 A    8/1987  Haber
5,286,261 A    2/1994  Roizenblatt
(Continued)

OTHER PUBLICATIONS

Richards Grayson, A.C., et al., Multi-pulse drug delivery from a resorbable polymeric microchip device, Nat. Mater., 2003; 2: 767-772.
(Continued)

*Primary Examiner* — Bhisma Mehta
*Assistant Examiner* — Matthew A Engel
(74) *Attorney, Agent, or Firm* — Rosenberg, Klein & Lee

(57) ABSTRACT

A subcutaneous implant system is applicable in a variety of surgical procedures and includes a balloon shaped implant formed from a bioresorbable material and is capable of assuming deflated and inflated configurations. The balloon shaped implant is inserted, in its deflated configuration, into the patient's body, and subsequently is inflated by filling the balloon shaped implant with a medicinal agent. The balloon shaped implant filled with the medicinal agent remains in the body and permits a steady-state release of the medicinal agent therefrom. The balloon shaped implant has a wall which may be formed from either a solid material which is impermeable to the medicinal agent, or a porous material. The medicinal agent egresses from the interior of the balloon shaped member in a controlled manner provided by a mechanism which may include a permeable membrane, a check valve, a flap valve, openings in a porous wall of the balloon shaped member, and combinations thereof. Upon the medicinal agent has been depleted, the balloon shaped implant is "naturally removed" from the body through bio-dissolution in the patient's body.

9 Claims, 22 Drawing Sheets

(56) References Cited

U.S. PATENT DOCUMENTS

| | | |
|---|---|---|
| 6,296,632 B1 | 10/2001 | Luscher et al. |
| 7,527,621 B2 | 5/2009 | Greenberg |
| 9,445,941 B2 | 9/2016 | Benner et al. |
| 9,452,083 B2 | 9/2016 | Benner et al. |
| 2005/0245906 A1* | 11/2005 | Makower et al. |
| 2006/0058891 A1 | 3/2006 | Kesh |
| 2010/0114074 A1 | 5/2010 | Perry et al. |
| 2015/0133896 A1 | 5/2015 | Benner et al. |

OTHER PUBLICATIONS

Kim, G.Y, et al., Resorbable polymer microchips releasing BCNU inhibit tumor growth in the rat 9L flank model, J. Controlled Release, 2007; 123: 172-178.

Richards Grayson, A.C., et al., Molecular release from a polymeric microreservoir device: Influence of chemistry, polymer swelling, and loading on device performance, J. Biomed Mater Res, 2004; 69A: 502-512.

London, N.J.S., et al., Temporary Scleral Buckle in Retinal Reattachment, Retinal Physician, Jul./Aug. 2014; 11: 42, 44, 46, 47.

Communication of an International Search Report From PCT/ISA/US Regarding a Counterpart PCT Application dated Oct. 6, 2017.

* cited by examiner

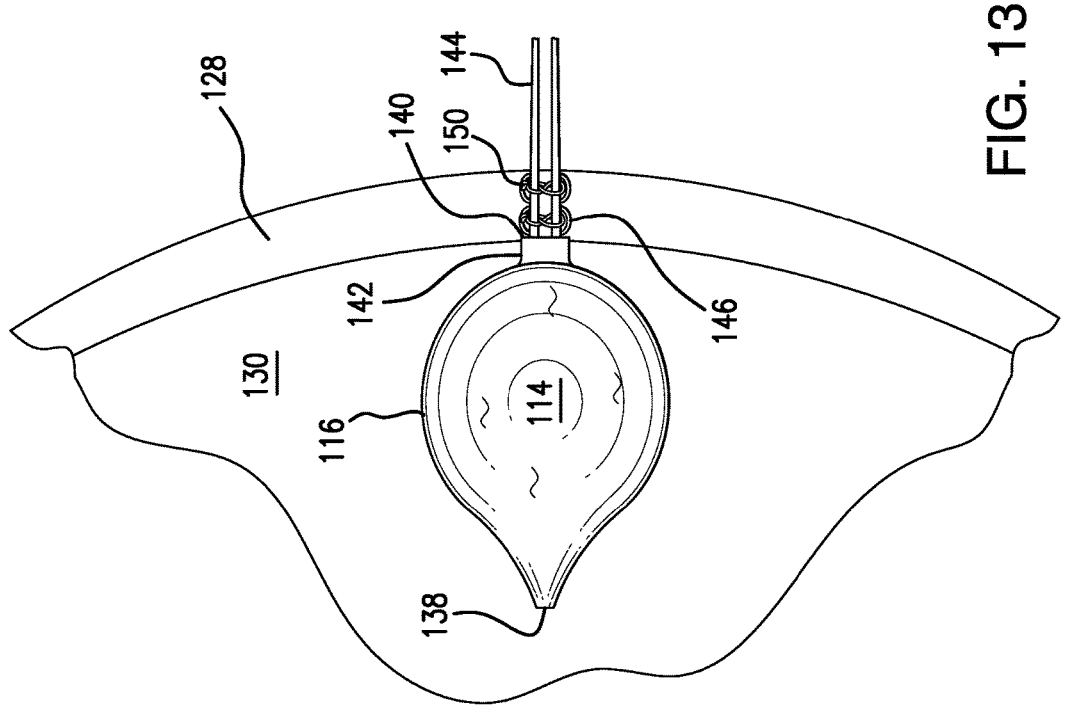

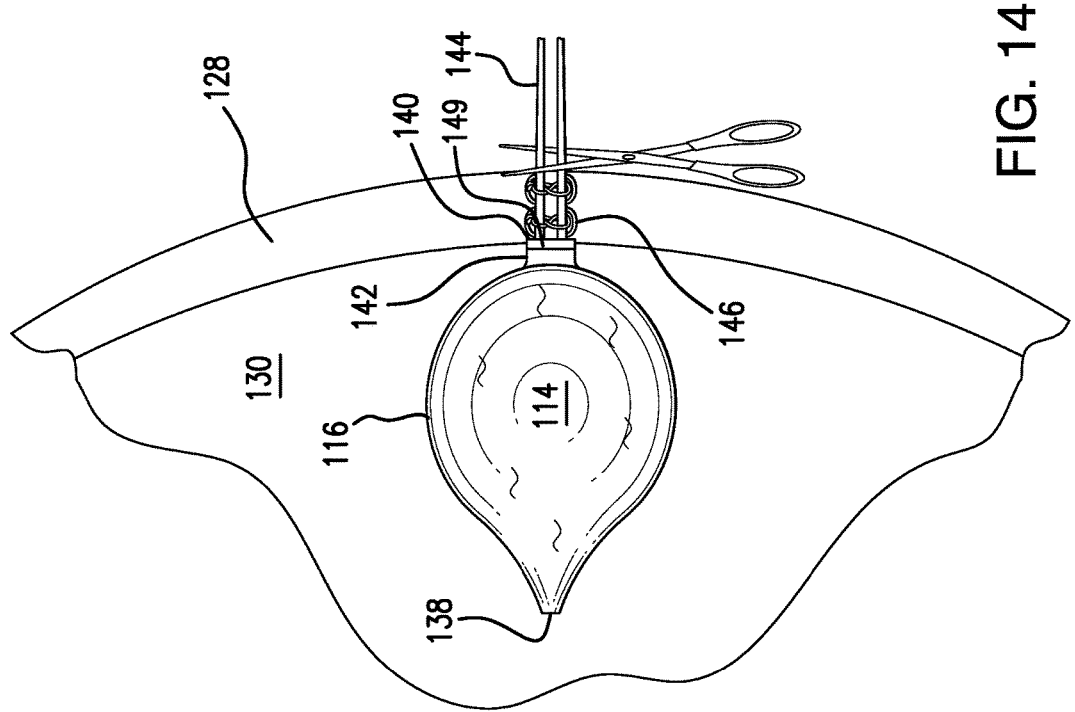

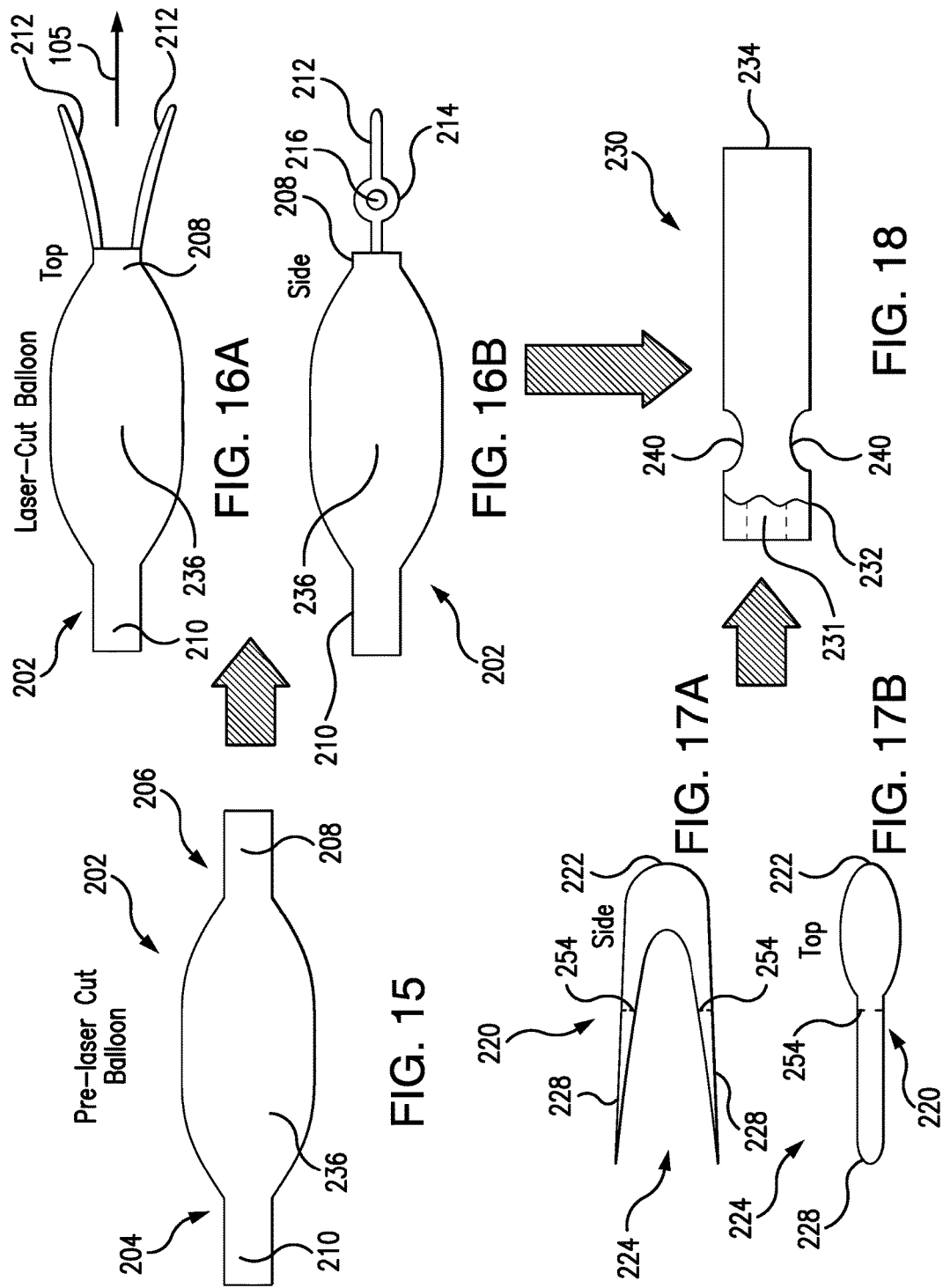

SUB-CUTANEOUS MEDICINAL DOSAGE DELIVERY IMPLANT SYSTEM

REFERENCE TO RELATED APPLICATION(S)

This Utility Patent Application is based on the Provisional Patent Application No. 62/377,092 filed on 19 Aug. 2016.

FIELD OF THE INVENTION

In overall concept, the subject system is directed to a bioresorbable implant system for sub-cutaneous, and/or sub-dermal, implantation of medicinal dosages in a joint space, bladder, GI tract, vitreous eye cavity, or other potential areas within the body of a patient.

The subject invention is additionally directed to systems and methods for treating a multiplicity of eye disorders and diseases by administering a therapeutic medium, medicinal drug or other agent, into the vitreous cavity of a patient's eye, and in particular, to implant systems which are adapted for insertion into the body of a patient for medical treatment purposes.

Further, the present invention is directed to the field of bioresorbable implants inserted into the body of a patient for a drug (or working fluid) elution into the patient's body, and configured to adequately control the dosage of a medicinal fluid or working fluid delivery into the patient's body.

The present invention is additionally directed to an implant system using a bioresorbable balloon member (formed from either solid impermeable material or from a porous material) implanted in the body of a patient adapted for delivery of a medicinal agent expelled therefrom in a controlled fashion, where the balloon member is designed in cooperation with a self-deploying valve to prevent undesirable leakage of the medicinal agent therefrom.

The subject invention is further directed to a system for treating a wide number of ophthalmological disorders or diseases, including, but not limited to, diseases of the retina, retinal pigment epithelium and choroid, by using a drug-eluting bioresorbable intravitreal implant through which therapeutic agents are administered intravitreally for subsequent diffusion through the tissues of the eye over an extended period of time to localize the action of the therapeutic medium in a desired portion of the eye under treatment.

In addition, the subject invention is directed to the field of administering therapeutic or medicinal agents to the tissues of the eye so that the pharmacodynamic action of the medicinal drugs may be localized at the choroid, retina, ciliary body or other areas of the eye.

Additionally, the subject invention is directed to an ophthalmic procedure using a balloon implantable into the Tenon space in proximity to the detached retina and filled with a working fluid to displace the sclera towards the detached retina to create and maintain contiguous contact therebetween for a predetermined period of time sufficient for healing and re-attachment of the retina to the retinal pigment epithelium of a patient's eye under treatment.

BACKGROUND OF THE INVENTION

A number of diseases may be effectively treated if a sustained delivery of a medicinal drug (also referred to herein as a therapeutic medium, therapeutic agent, or medicinal agent) is provided in accordance with a protocol (medicine dosage and the schedule of administering the medicine) recommended by a treating physician. Unfortunately, patients' non-compliance with taking their medications usually undermines the efficiency and outcome of medical treatment. In other words, prescribed medications will hardly work in patients who either do not take them or fail to follow a recommended regimen (protocol or schedule) of medications intake.

Some conventional implant systems utilize a concept of delivering a deflated balloon into a cavity of a patient's body and subsequent inflating of the balloon to anchor the balloon in place. Such common procedures are found in angioplasty, and other procedures. However, these systems do not use the anchored balloon filled with a medicinal agent for subsequent expelling into the body of a patient. These systems do not use a bioresorbable composition for balloon implant fabrication, since such requires the inflated balloon to remain in place intact, especially in case of angioplasty or the like.

Most drug delivery implant systems use Non-resorbable Drug Delivery Systems (DDSs), such as, for example, inflated balloons (generally used for unblocking veins), which are removed at the end of the procedure to provide a cleared pathway for blood flow.

The non-resorbable sub-cutaneous drug delivery system implants are produced by, for example, Debiotech, which fabricates a silicon nano-porous membrane system Debiostar, which delivers somatostatin.

Another drug delivery implant system, such as a DUROS implant platform, is designed with the implant for releasing leuproliode medicine for treating prostate cancer, as well as Exenatide (GLP-1 agonist) for treating type-2 diabetes, or pain medications. The DUROS uses a titanium implant DDS that is osmotically driven and provides "zero order" drug delivery.

Both Debiostar and DUROS must have their implants surgically removed after the drug "pay-load" has been delivered.

The Robert Langer Laboratory at MIT has developed a resorbable multi-reservoir (36 reservoirs) DDS fabricated from poly (L-lactide) and PLGA membranes of different molecular masses, each for covering a respective one of 36 reservoirs that releases pulses of different drugs at intervals after the implantation procedure.

This is, however, a somewhat complex and expensive implant system requiring several types of bioresorbable polymers (of different molecular masses) mixed (or impregnated) with respective medicinal agents to be fabricated in a single implant.

In addition, this system is fabricated with the medicinal agent(s) pre-loaded in the implant prior to the implantation in the body of a patient, which requires a sufficient receiving volume to retain the medicinal agents. Microchips as large as ~1.2 cm in diameter are fabricated which are pre-loaded with medicinal agents. The dimensions of the MIT's implant exceeds a desired range appropriate for a sub-cutaneous implantation procedure.

Numerous eye disorders may permanently damage vision in an affected eye and possibly lead to blindness if untreated. Such vision threatening disorders include, for example, ocular neovascularization, ocular inflammation, retinal degeneration, and retinal detachment.

Various diseases of the eye have been conventionally treated by injection directly through the sclera of a medicinal drug composition. This approach limits effective delivery of therapeutic medium to the retina/choroid when the therapeutic medium is injected directly into the vitreous, and fails to provide for a sustained therapy for the target tissue.

Additionally, such prior art procedures, do not permit the maintenance of the medicinal drug in a relatively stable position within the vitreous and may produce side effects associated with the injection of drugs directly. Prior art procedures either allow the device to be free floating in the vitreous cavity or the device is anchored to the eye wall with an external element that protrudes outside of the sclera. The protruded element poses a risk for erosion/extrusion of the device and infection of the patient's eye.

Thus, there is a longlasting need for a device or system that can overcome this non-compliance issue by providing an uninterrupted and steady-state release of a drug or a medicinal agent in a patient's body over an extended period of time as prescribed by physician. Such a device (or system) should be able to provide sustained delivery of a medicinal drug at a predetermined dosage level to a specific organ (or part of the body) or provide systemic delivery of the drug or medicinal agent throughout the entire body of the patient. Ideally, such a device (or system) is to be inert to tissues and fluids of the body, non-inflammatory, and bioresorbable, that is, should dissolve without a trace after the medicinal agent (or drug) has been completely released into the patient's body or a specific organ.

A number of diseases require the attachment-and-reattachment of a patient's tissue to other tissues of the patient, such as, for example, in treatment of retina detachment. In traditionally performed ophthalmic procedures, systems for treating retina detachment provide for a band to be positioned surgically around the sclera of the eye to force or displace the sclera into contact with the retina, and a scleral buckle (or band) is permanently sewn to the globe.

However, such traditional ophthalmic procedures are location sensitive and are not capable of providing a continuous interface of the retina with the sclera. In addition, this approach is prone to cause several disadvantageous outcomes including induced myopia (nearsightedness), erosion/extrusion of the band potentially leading to infection, double vision, and chronic eye pain.

In an effort to circumvent these problems, a temporary and removable scleral buckle has been introduced in the field of ophthalmic surgeries. These devices are implanted for a predetermined time duration, and subsequently are removed in a separate surgical procedure. One of these devices is what is commonly known as the Lincoff buckle.

Other prior devices (such as that described, for example, in U.S. Pat. No. 5,286,261) are designed for correcting retinal detachments by heat shrinking of a scleral band for scleral indentation over a tear region.

More recently Tornambe developed a solid version of a temporary scleral buckle which is removed in a separate surgical procedure three weeks after attachment of the scleral buckle, as referenced in "Retinal Physician," Jul. 1, 2014, London, N J S, Tornambe P E. Clearly, the need for an additional surgical procedure to remove the implant post-operationally is a disadvantage of such an approach.

Therefore, there is a need for a temporary scleral buckle that indents the eye wall/sclera long enough to reattach the retina, and which subsequently can completely reabsorb, thus avoiding the need for additional surgery.

Some prior art systems (such as that described, for example, in U.S. Patent Application Publication No. 2010/0114074) are directed to delivery systems for release of an active agent to body cavities for a predetermined administration time period. However such systems are extraneous to a concept of insertion of an active (therapeutical) agent into a bioresorbable balloon-like member implanted in the body for permitting the active agent to be dispersed in the patient's body (or an organ) from the balloon-like member over a period of time. In addition, the conventional delivery systems do not address absorption of the implanted member into the patient's body.

In general, it is a long-lasting need in the surgical art for a sub-cutaneous drug delivery implant system which would be fully bio-resorbable in the patient's body after the medicinal agent has been delivered, and which would be small enough for ease of implantation and comfort of the patient, and which would be fabricated through a simple and inexpensive manufacturing process.

SUMMARY OF THE INVENTION

It is, therefore, an object of the present invention to provide a medicinal agent eluting intravitreal implant system which dispenses a medicinal agent sub-cutaneously into a patient's body (such as, for example, in the vitreous cavity of the eye, in a joint space, bladder, GI tract, or other areas within the body of a patient) in a controlled manner over a period of time.

It is a further object of the present invention to provide a bioresorbable implant (formed from a porous material or from a solid material devoid of pores) that is filled with a medicinal composition, inserted and anchored within a space in a patient's body for a steady delivery of the medicinal composition to the organ(s) under treatment, and which is dissolved in the patient's body subsequent to the dispersing of the entire volume of the medicinal composition from the implant.

It is another object of the present invention to provide an implant system and method for treatment and prevention of disorders (or diseases) of eyes, in particular, retinal/choroidal disorders or diseases, through an intravitreal administration or intravitreal prophylactic administration of a therapeutic medium, and delivering a therapeutic medium to an interior segment of a patient's eye, where the therapeutic medium may include, but is not limited to, drugs, medicaments, antibiotics, antibacterials, antiproliferatives, neuroprotectives, anti-inflammatories (steroidal and non-steroidal), growth factors, neurotropic factors, antiangiogenics, thrombobolytics, antibodies, biologics as well as genes.

In addition, it is an object of the present invention to provide the process of disposing of a therapeutic amount of therapeutic medium intravitreally (or into the intravitreal space), and more specifically, to localize the action of the therapeutic medium at the choroid and the retina of the eye.

It is a further object of the present invention to provide an ophthalmic system and procedure for inserting a working fluid into a bioresorbable balloon which is inserted into a body cavity of a patient in order to administer a therapeutic or medicinal agent to facilitate a beneficial effect either locally or systemically throughout the body of a patient.

It is also an object of the present invention to provide an ophthalmic procedure using a bioresorbable balloon member implantable into the Tenon space in proximity to the detached retina to displace the sclera towards the detached retina to maintain contiguous contact therebetween for a predetermined period of time to allow reattachment of the retina to the retinal pigment epithelium.

It is another object of the present invention to provide an implant system which may be quickly inserted through the sclera of a patient's eye with a reduced time for the overall procedure being accomplished, and where the medicinal drug is contained within a biodegradable enclosure which dissolves in the patient's eye after the drug is released therefrom into the patient's eye.

It is a further object of the present invention to provide an implant system which can be actuated by a pneumatic drive system to adequately control the dosage of a medicinal fluid (or working fluid) into a cavity in the patient's body.

Furthermore, it is an object of the present invention to provide an implant system equipped with a check or flap-valve which is placed over the opening of the proximal neck of the implantable balloon shaped member in such a manner that it partially (or completely) closes the opening of the proximal neck. The flap-valve may be composed of a selectively-permeable material (membrane) that will allow the release of the drug (or medicinal composition) from the implanted balloon shaped member in such a manner as to extend the duration of the drug delivery.

It is also an object of the present invention to provide an implant system and method equipped with a self-deploying valve member that is designed to prevent the collapse of the balloon implant or loss of the medicinal fluid from the interior of the balloon implant. The self-deploying valve member is attached to and closes (seals) the end of an injection needle (injection tube) that resides inside of the collapsed balloon, until such time that the balloon implant (anchored in the patient's body) is inflated with the medicinal fluid through the injection tube. After the balloon implant is inflated, the injection needle is withdrawn from the balloon implant. The retraction of the injection needle causes wedging of the valve into the proximal neck of the balloon implant, thereby effectively sealing the proximal end of the balloon implant. A portion of the valve that is attached to the needle either tears away from the now-wedged portion of the valve by its perforations or is cut away by the surgeon. The self-deploying valve occludes the balloon neck, which prevents the leakage of the medicinal fluid from the balloon implant. In this implementation, the balloon's wall is formed from a porous material so that the medicinal agent escapes through the holes (pores) in the balloon's wall.

It is an additional object of the present invention to provide an implant system which reduces side effects which would be typically associated with the injection of drugs directly into the vitreous.

In one aspect of the invention, a bioresorbable drug eluting intravitreal implant system includes a syringe with a chamber adapted to contain a medicinal drug (agent). The syringe is equipped with a displaceable plunger for transporting the medicinal drug external to the syringe from a syringe chamber and a closed-tip injection tube (injection needle) which is formed into a distal end section, a central section, and a proximal section.

A balloon member is fabricated from a bio-resorbable composition and is releasably secured to the needle's distal end section and the needle's proximal section. The needle's central section has a central section chamber in fluid communication with the syringe chamber. The needle central section has an opening formed through its wall for transport of the medicinal drug to an interior section of the balloon.

The subject concept also relates to the method of implanting a bioresorbable drug into the patient's body, for example, the eye of the patient. The method provides a bioresorbable balloon shaped member having proximal/distal ends. The balloon shaped member includes a through opening extending from the proximal end to the distal end. The balloon shaped member is mounted over a needle member which in itself is formed with a distal section, a central section, and a proximal section. The distal end of the balloon is closed.

The subject system includes a balloon transport mechanism to implant the balloon member into a patient's eye, and a medicinal agent transport mechanism (formed with a syringe plunger) to transport the medicinal agent from the syringe chamber into the balloon member implanted in the patient's eye by the balloon transport mechanism. The needle member serves as the balloon transport mechanism for implanting the balloon member into the patient's eye. The needle also constitutes a portion of the medicinal agent transport mechanism as it provides a passage for the medicinal agent from the syringe chamber into the balloon member.

The balloon shaped member is positioned in a releasable contact with the distal end section and the proximal section of the needle shaped member. The needle member is then inserted through the sclera of a patient's eye to a predetermined depth, and the balloon shaped member is subsequently inflated with a medicinal drug transported by the medicinal agents transport mechanism from the syringe through a flow channel into a central section chamber and through at least one side opening formed through the needle central section to inflate the balloon shaped member with the medicinal drug (agent). The medicinal agent transport mechanism may be configured with a plunger controllably displaceable within the syringe to transport the medicinal agent from the syringe chamber into the balloon member through the side opening formed in the needle member after the balloon member has been implanted in the patient's eye by the needle member (balloon transport mechanism).

The balloon shaped member may be formed into an ellipsoidal, spheroidal, cylindrical, or any other geometrical contour as the result of inflation of the balloon shaped member with the medicinal drug subsequent to placement of the deflated balloon shaped member into the patient's body. In the case of implantation into the vitreous cavity, the ellipsoidal (or somewhat spheroidal) contouring of the balloon shaped member provides for a stable positioning of the balloon shaped member in the vitreous cavity and conforms to the vitreous cavity contour in an optimized manner.

Subsequent to inflation of the balloon shaped member with the medicinal drug, the needle is then withdrawn from the interior of the patient's eye and the balloon shaped member may be maintained within the eye interior through suturing or some like technique.

Preferably, a flap-valve membrane of other type check valve is placed over the opening of the proximal neck of the balloon shaped member in such a way that it partially or completely closes the opening of the proximal neck. This flap-valve may composed of a selectively-permeable material (membrane) that will allow the release of the drug (or medicinal composition) in such a way as extend the time duration of the drug delivery.

In one of the embodiments, the subject system and method use a self-deploying valve (plug) that operates to prevent the collapse of the balloon shaped member or loss of the medicinal agent from the interior thereof. The self-deploying valve is attached to and seals the end of the injection needle. The injection needle is brought into the collapsed balloon shaped member, and both are inserted in the patient's body. Subsequently, the balloon shaped member is inflated with the medicinal agent (following the insertion of the needle with the collapsed balloon attached thereon into the patient's body).

After the balloon shaped member has been inflated with the medicinal agent through the opening(s) formed at the needle's central section, the injection needle is withdrawn, causing the plug attached to the distal end of the injection needle to move therealong towards the proximal end of the balloon and wedging of the self-deploying valve into the proximal portion neck of the inflated balloon-shaped inflated member, thus sealing the proximal end thereof.

A portion of the self-deploying valve that extends externally the balloon shaped member may be either torn away from the now-wedged valve (along its perforations) or be cut away by the surgeon.

The valve occludes the balloon's proximal portion neck, and thus prevents leakage of the medicinal fluid from the balloon implant. In the embodiment, where the distal end of the balloon is sealed, and the proximal end of the balloon is occluded by the self-deploying plug, the medicinal agent may discharge itself from the balloon implant through the walls of the balloon member manufactured from a porous material to extend the duration of the therapy.

The proximal neck section may be further altered to transform into a set of anchor fixation struts formed with loops that enable the fixation of the inflated/filled balloon shaped member to the sclera/eye wall with a suture. The long arms of the fixation struts are used to manipulate and position the filled balloon while placing the fixation sutures in the sclera. After the suture is tied, the long arms are cut-off flush with the sclera.

At the end of the procedure the inflated balloon shaped member and the anchor strut are secure and completely hidden in the interior of the eye, including the suture knot which is buried within the sclera.

In another aspect, the present invention is particularly directed to the ophthalmic procedure for treatment of retinal detachment, during which a flexible or rigid tube (or cannula) is inserted into Tenon's space of the patient's eye. The flexible or rigid tube is coupled in fluid communication with and between a syringe containing a working fluid and an implant balloon to be inflated with a working fluid subsequent to its placement in the patient's eye. The balloon is positionally located in proximity to the area of the retina detachment and is inflated with the working fluid to displace the sclera into contact with the retina. After a predetermined time period, the balloon and the working fluid resorb.

In still another aspect of the invention, the subject system and method may be adapted to providing a procedure for differing organs of a patient's body where it is desired to administer a therapeutic (or medicinal) agent to facilitate a beneficial effect either locally or systemically throughout the body of a patient.

BRIEF DESCRIPTION OF THE DRAWINGS

FIG. 13 is a schematic view of the subject implant system embodiment showing the inflated balloon shaped member sutured to the patient's eye;

FIG. 14 is a schematic view of the subject implant embodiment showing the subject ophthalmic technique showing the cutting and securement of the inflated balloon shaped member to the sclera of the patient's eye;

FIG. 15 is a perspective view of the subject balloon shaped member in another embodiment of the present system;

FIGS. 16A-16B show a modified balloon shaped member by laser cutting the balloon shown in FIG. 15, where FIG. 16A is representative of the top view of the modified balloon shaped member, and FIG. 16B is a side view of the laser cut modified balloon shaped member;

FIGS. 17A-17B are representative of the laser cut plug used in the alternative embodiment of the present system, where FIG. 17A is a side view of the laser cut plug, and FIG. 17B is a top view of the laser cut plug;

FIG. 18 shows schematically the injection tube (also referred to herein as an injection needle) used in the subject system;

DESCRIPTION OF THE PREFERRED EMBODIMENTS

The subject implant system as herein described, is shown and adapted to be utilized in various therapeutical procedures, and may be used in a variety of embodiments for different organs of the human's body, such as, for example, subcutaneously, in a joint space such as a synovial capsule, in a bladder, or a GI tract, such as the gut or esophagus, or stomach, etc. However, for the sake of clarity and as an example, the subject implant system and method will be described herein as adapted for use in opthalmological procedures.

Referring now to FIGS. 1-6, the subject bioresorbable drug eluting intravitreal implant system (hereinafter also referred to herein as an implant system) 10, is composed of a syringe 14, a needle member 20, and a balloon shaped member 22 which will be detailed in following paragraphs.

The subject system is equipped with a balloon transport mechanism for implanting the balloon shaped member into the patient's eye, and a medicinal agent transport mechanism for filling the balloon member (after it has been implanted into the patient's eye) with the medicinal agent transported from the syringe into the implanted balloon member. Both transport mechanisms will be detailed in further paragraphs.

Figure 1:
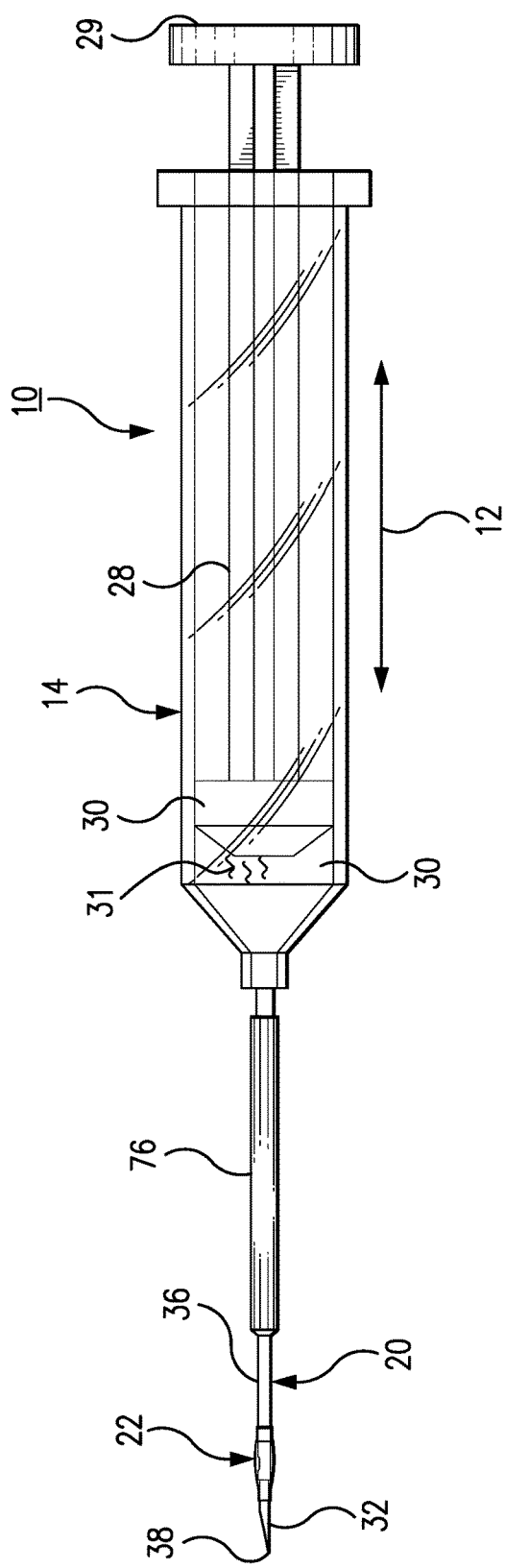
FIG. 1 is an elevational view of the subject bioresorbable intravitreal implant system.
Figure 6:
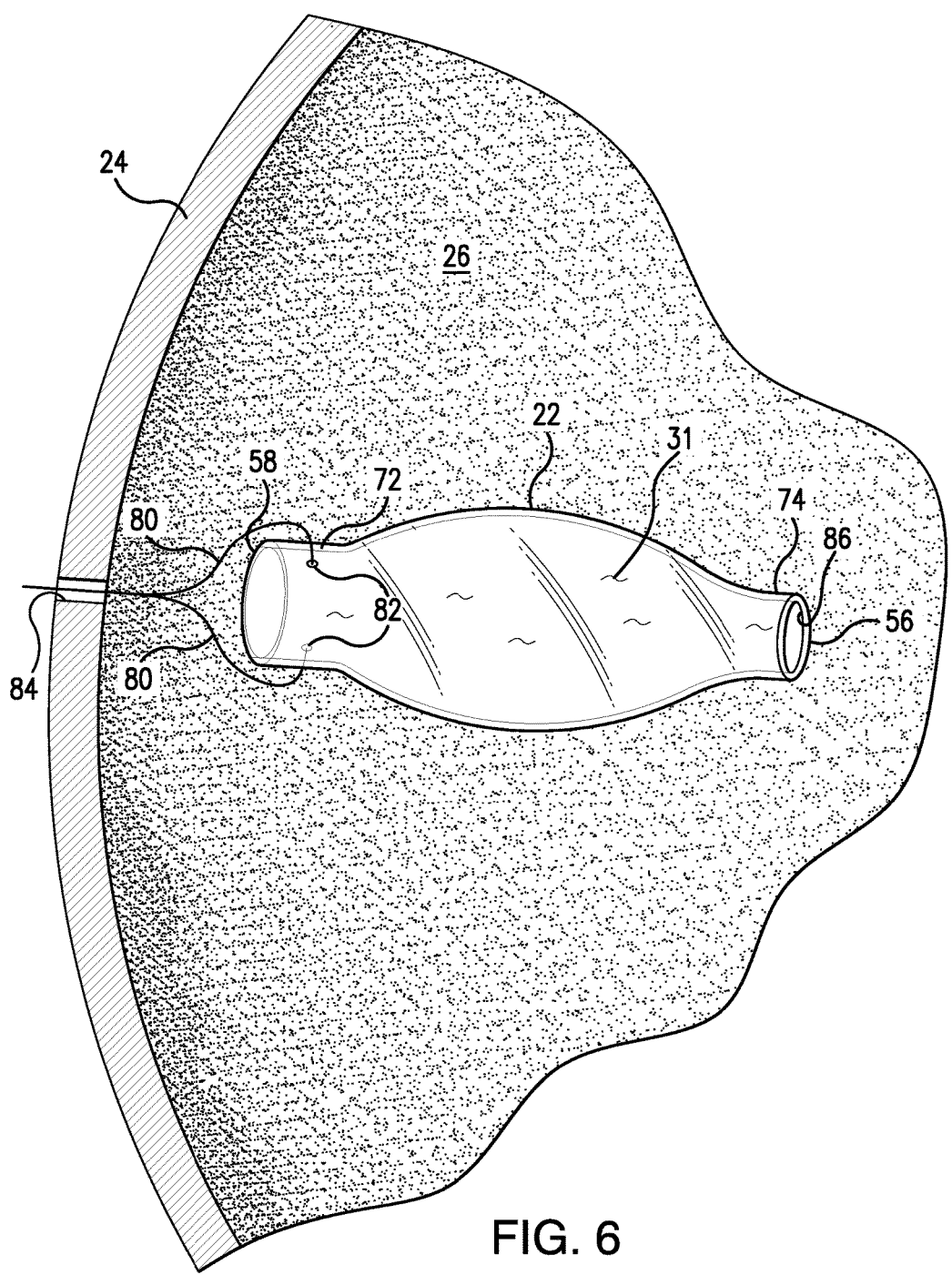
FIG. 6 is a schematic representation of the subject balloon shaped member within the eye of the patient being secured by sutures.

The syringe 14 may be a standard surgical syringe formed of a plastic composition, not important to the inventive concept as herein described, with the exception that it should be operable to transport a medicinal drug into balloon shaped member 22 which is adapted for implantation within an internal portion of the eye 26 in an ophthalmic procedure, as seen in FIG. 6. The syringe 14 extends in the longitudinal direction 12 as seen in FIG. 1.

The syringe 14 is equipped with a plunger 28 which includes a syringe head 29 manually displaced by a surgeon during an implant procedure. The plunger also may be pneumatically actuated, as will be described in other embodiments of the subject implant system.

The syringe 14 is formed with a syringe chamber 30 which contains a medicinal drug (agent) 31 (or other therapeutic agent or working fluid) to be used during a surgical procedure and treatment. During the procedure, the syringe chamber 30 is disposed externally to a patient's body, and is referred to herein also as an external chamber.

In operation, the medicinal agent transport mechanism is actuated with the plunger 28 is displaced in the longitudinal direction 12 to create a force against the medicinal drug (agent, or working fluid) 31 contained within the syringe chamber (external chamber) 30 to force the medicinal drug 31 to be transported external the syringe 14, as will be described in the following paragraphs. Thus, the syringe 14 has the chamber 30 adapted to contain the medicinal drug and uses the displaceable plunger 28 for transmission of the medicinal drug from syringe 14. The plunger 28 which is controllably displaceable (actuatable) within the syringe 14, serves as a medicinal agent transport mechanism for transporting the medicinal agent 31 from the syringe chamber (external chamber) 30 into the balloon member 22 after it has been implanted into the patient's eye, as will be detailed in the following paragraphs.

Figure 4:
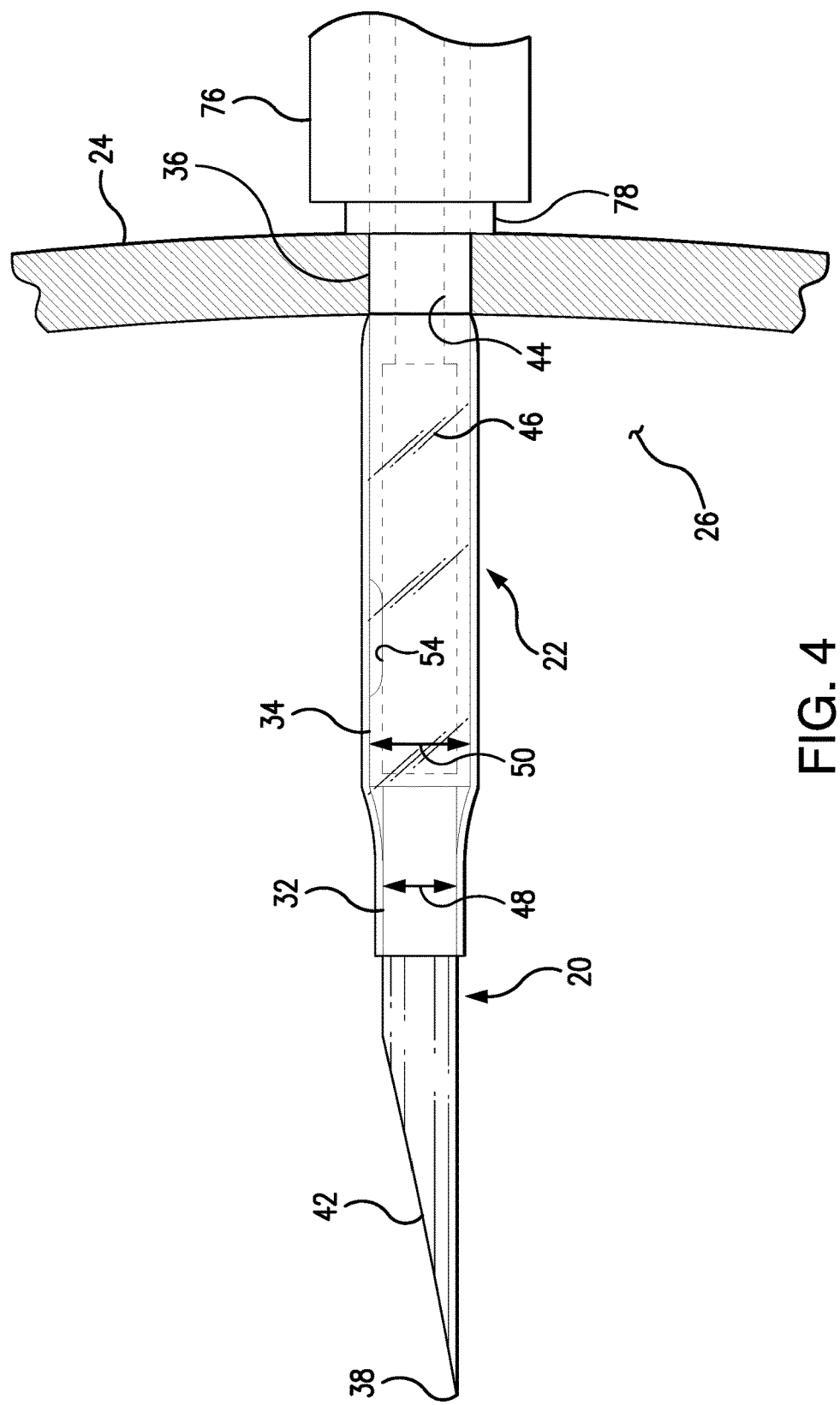
FIG. 4 is an elevational view of a portion of the subject implant system when inserted into the interior of the patient's eye prior to inflation of a balloon containing a therapeutic medium.
Figure 5:
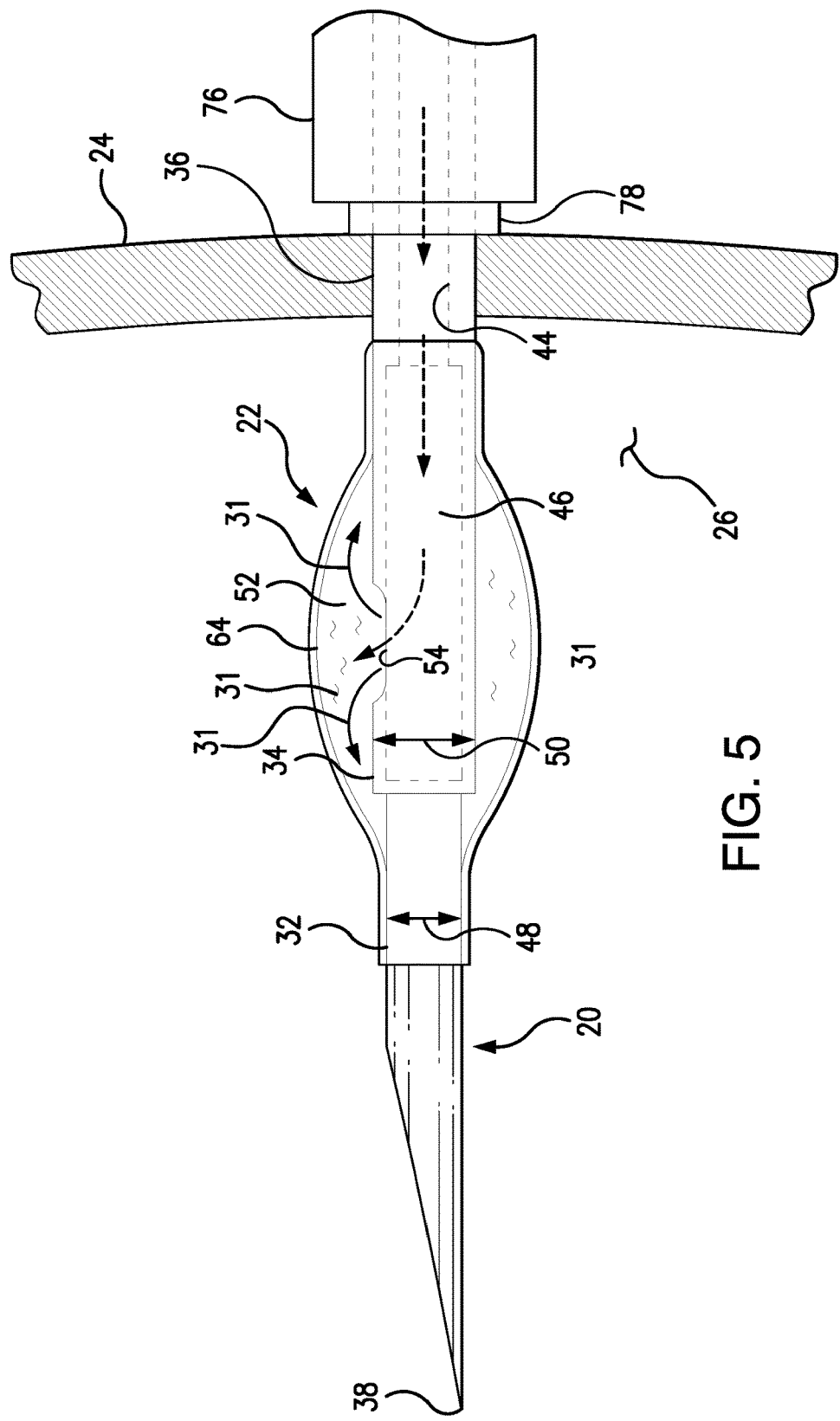
FIG. 5 is an elevational view of a portion of the subject implant system showing the inflation of the balloon shaped member with the medicinal drug subsequent to the implanting procedure but prior to removal of the needle (injection tube) from the interior of the patient's eye.

The needle (also referred to herein as a tabularly shaped injection member) 20, as more clearly seen in FIGS. 4 and 5, includes a needle distal section (also referred to herein as a closed distal section) 32, a needle central section 34, and a needle proximal section 36. The closed distal section 32 of the needle 20 includes a needle point 38 or a blunt closed end (to be described in other embodiments of the subject implant system) formed at one end of the needle distal section 32.

Figure 3:
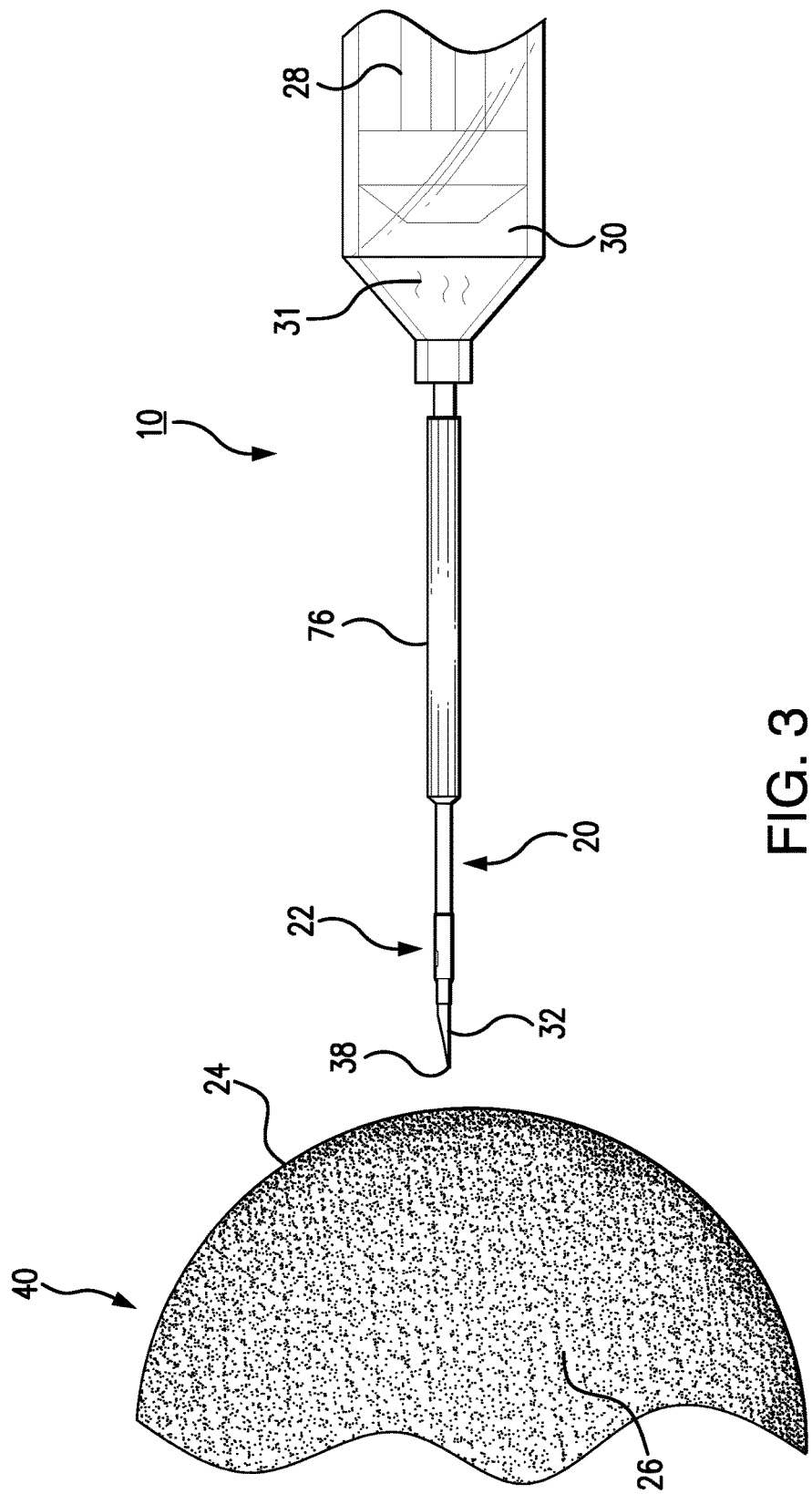
FIG. 3 is an elevational view of the subject bioresorbable drug eluting intravitreal implant system prior to insertion through the sclera of a patient's eye.

As shown in FIG. 3, during the surgical procedure, the needle (tubularly shaped injection member) 20 is inserted through the sclera 24 of the eye to serve as a balloon transport mechanism for the balloon shaped member 22 to permit placement of the balloon shaped member 22 into the interior 26 of the patient's eye. The tubularly shaped injection member 20 is intermittently referred to herein as a balloon transport mechanism as it serves for transporting the balloon shaped member 22 into the patient's eye.

The diameter of the needle distal section 32 is formed as small as possible for insert through the sclera 24 but of a sufficient diameter for transport and placement of the balloon shaped member 22 into the vitreous cavity of the patient's eye 40. The needle distal section 32 includes a tapered section 42 (or blunt closed end) for ease of a passage through the sclera 24 to the internal portion 26 of eye 40.

In overall concept, in one embodiment of the implant system 10, the needle 20 (formed with the needle distal section 32, the needle central section 34, and the needle proximal section 36) is used as the basic balloon transport mechanism for introducing the balloon shaped member 22 into the internal portion 26 of eye 40.

The needle distal section 32 is formed somewhat in a rod-like structure and contains no through opening whether the needle distal section is a tapered closed end section or a blunt closed end section.

As is further shown in FIGS. 4 and 5, the proximal section 36 and the needle central section 34 include a flow channel 44 for insert of a medicinal drug 31 into the needle central section chamber 46 for transport of the medicinal drug internal to the balloon shaped member 22, as is seen in FIG. 5. The needle distal section 32 has a diameter 48 which is smaller than the needle central section diameter 50. In this fashion, a shoulder is created between the needle distal section 32 and the needle central section 34, as is shown in FIGS. 4 and 5.

As the plunger 28 is displaced in the longitudinal direction 12, the medicinal drug 31 contained within the syringe chamber 30 is transported through the flow channel 44 into the needle central section chamber 46 (as shown in FIG. 4), and is adapted to be further transported to an interior section 52 of the balloon shaped member 22, as is shown in FIG. 5. In order to provide fluid communication from the needle central chamber 46 to the interior 52 of the balloon shaped member 22, an opening 54 is formed in a wall of the needle central section 34. It is to be understood that the opening 54 may be a singular opening 54 or in the manner of a plurality of openings 54 formed through a circumferential surface of the needle central section 34.

Thus, the medicinal drug 31 is transported from the syringe chamber 30 through the flow channel 44 into the needle central section chamber 46 and exits from the opening 54 into the interior 52 of the balloon shaped member 22.

Figure 2:
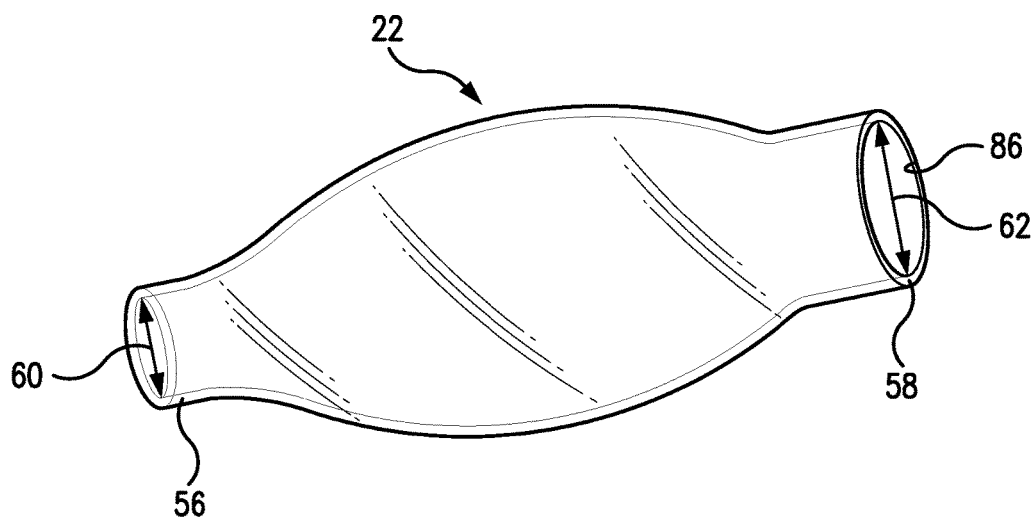
FIG. 2 is a perspective view of the subject balloon shaped member containing a medicinal drug.

Prior to being implanted in the eye 40, the balloon shaped member 22, in its deflated configuration, is mounted on the needle member (which constitutes the balloon transport mechanism). Specifically, the balloon member 22 is mounted over the needle central section 34 and the needle distal section 32. In order to accommodate the mounting of the balloon shaped member 22 on the needle distal section 32 and the needle central section 34, the balloon shaped member 22 has opposing distal end 56 and proximal end 58, as is shown in FIG. 2. The balloon distal end inner diameter 60 is smaller than the balloon proximal end inner diameter 62 to permit accommodation of mounting of the balloon proximal end 58 on the needle central section 34 and needle proximal section 36 while permitting mounting of the balloon distal end 56 on the needle distal section 32. The balloon shaped member 22 is shown in FIG. 2 in at least a partially inflated state for illustrative purposes in order to explain the sizing of the balloon shaped member 22.

The balloon shaped member 22 is formed of a substantially elastic and biodegradable (bioresorbable) composition which can be absorbed into the patient's body subsequent to implantation of the balloon shaped member 22 within the internal portion of eye 26. In one implementation, the balloon shaped member's wall may be formed as a layer of a solid material which is impermeable to the medicinal agent filling the balloon, so that the medicinal agent cannot escape from the balloon's interior via its wall. This embodiment is particularly applicable to the balloon shaped member shown in FIGS. 2, 5, 6, 7, 9, 13, and 14.

In another embodiment, the balloon's wall, or at least a portion of the balloon's wall, is formed from a porous material which permits the egress of the medicinal agent through pores (openings) formed in the balloon's wall. This embodiment is particularly applicable to the balloon-shaped member shown in FIGS. 21-22, where the distal and proximal ends of the balloon-shaped member are closed.

In the deflated condition of the balloon shaped member 22, as is seen in FIGS. 1 and 4, the balloon shaped member 22 is mounted over the needle distal section 32 and the needle central section 34 where the balloon shaped member 22 is substantially flush with, and abuts the needle central section 34, the needle distal section 32, and the needle proximal section 36.

Subsequent to the insertion of the needle 22 through the sclera 24, the medicinal agent transport mechanism is actuated (i.e., the plunger is displaced by a surgeon), so that the balloon shaped member 22 is inflated with the medicinal drug 31 exiting from the syringe chamber 30 under the plunger created pressure, as is seen in FIG. 5, prior to removal of the needle 22 from the internal portion 26 of eye 40.

The opening (or slot) 54 formed in the needle central section 34 is seen to be in alignment with the balloon central section 64 (as shown in FIG. 5) to allow transport of the medicinal drug 31 from the needle central section chamber 46 into the interior 52 of the balloon shaped member 22.

Figure 7:
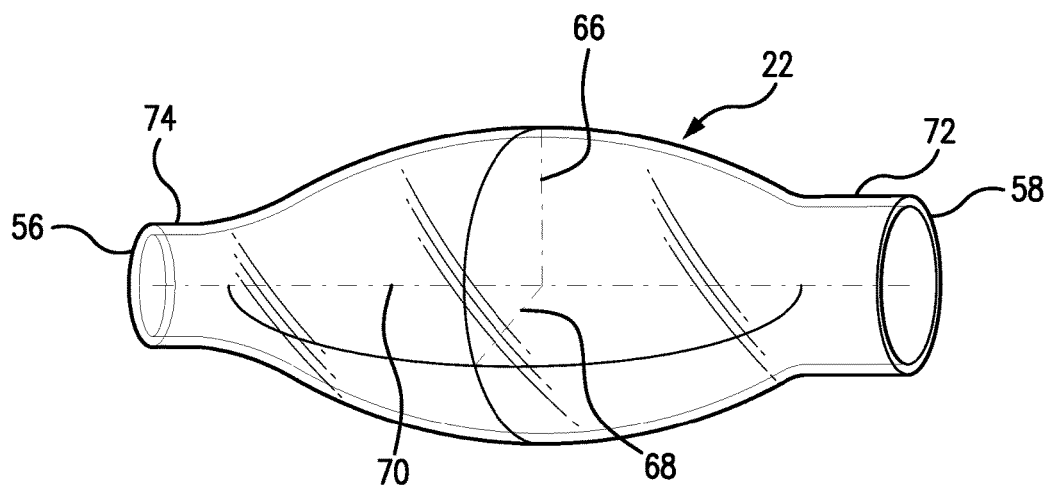
FIG. 7 is a schematic representation of the subject balloon shaped member showing dimensional characteristics for an ellipsoidal/spheroidal contour of the balloon shaped member.

In one of preferred embodiments, as seen in FIG. 7, when inflated, the balloon shaped member 22 assumes an ellipsoidal/spheroidal contour for optimization of the placement in the interior portion 26 of the eye 40. The balloon shaped member 22 includes a proximal neck section 72 and a distal neck section 74. When inflated, the balloon Z-axis radius 66 would approximate 3.0 mm, the balloon Y-axis radius 68 would, approximate, for example, 3.0 mm with the longitudinal or X-axis radius 70 approximating 4.0 mm. This dimensioning would provide for an approximate internal volume of the balloon shaped member 22 to be substantially 150 mm$^3$. In other applications adapted for various organs of the patient's body, the dimensions of the balloon shaped member may vary.

This optimum type of the balloon shaped member configuration is seen in FIG. 7 which provides for an optimization of the eluting the drug from the balloon shaped member 22 subsequent to its insertion into the interior 26 of the eye 40. Once inserted in the balloon shaped member implanted into the eye, the medicinal drug may be eluted from both the balloon distal end 56 and the balloon proximal end 58 in a controlled manner to provide therapeutic value to the patient over an extended period of time.

The subject implant system 10 further includes a sleeve member 76 which is slidably received on the needle proximal section 36 to aid in the removal of the needle 20 from the interior 26 of the eye 40. In this manner, the surgeon may grasp the sliding sleeve 76 and simply pull the syringe 14 including the needle 20 from the interior 26 of eye 40 while maintaining the balloon shaped member 22 containing the medicinal drug within interior 26, as is seen in FIG. 6.

A fixing member (or a stop member) 78 is secured to an end of the proximal end section 36. The stop member 78 has an external diameter which is greater than an outer diameter of the needle proximal section 36 and smaller than an outer diameter of the slidable sleeve member 76. In this manner, the depth of the balloon shaped member 22 within the interior 26 of the eye 40 may be controlled to ensure that the balloon shaped member 22 is accurately positioned during the ophthalmic procedure. Compositions of the sliding sleeve 76 and the stop member 78 are not important to the inventive concept of the subject implant system 10, with the exception that they be compatible with surgical room procedure requirements.

In some instances, the balloon shaped member 22 filled with the medicinal drug may be left within the interior 26 of the eye 40 without anchoring into place. However, in a preferred embodiment, the balloon shaped member 22 is somewhat fixedly positioned within the interior 26 of the eye 40 by the sutures 80, as seen in FIG. 6. The sutures 80 are fixed to the balloon proximal end section 72 at the suture fixing points 82 extend through the sclera slit 84 (enlarged for purposes of illustration) formed by the needle 20 upon insert through the sclera 24. In this manner, the medicinal drug 36 may be positionally located in a somewhat stable manner within the interior 26 of the eye 40. The medicinal drug 31 is eluted to the interior 26 of the eye 40 through the open balloon distal end 56 and the balloon proximal end 58.

The balloon shaped member 22 being formed of a biodegradable composition is absorbed into the body of the patient subsequent to the medicinal drug being dispersed over a period of time.

FIGS. 1-6 are descriptive of the subject procedure for implanting a bioresorbable drug 31 into the eye 40 of a patient. Initially, the balloon shaped member 22 formed of a biodegradable composition is established with the balloon shaped member 22 having the proximal end 58 and the distal end 56. The balloon shaped member 22 has a through opening 86 extending throughout the balloon length from the balloon distal end 56 to the balloon proximal end 58.

The balloon shaped member 22 is mounted over the needle 20 having the distal end section 32, the central section 34, and the needle proximal section 36. The balloon shaped member 22 is mounted in a releasable contact with the needle distal end section 32 and the needle proximal section 36.

Prior to insertion of the needle 20 through the sclera 24, the balloon shaped member 22 is snugly mounted to and is substantially in contiguous contact throughout its length with the needle distal section 32 and the needle central section 34 as well as the needle proximal section 36.

The needle member 20 (which serves as the balloon transport mechanism) is then inserted through the sclera 24 of the eye 40 to a predetermined depth. The balloon shaped member 22 is then inflated (by actuating the medicinal agent transport mechanism through displacement f the plunger 28) with the medicinal drug 31 being transported from the needle central section 34 to the interior 52 of the balloon shaped member 22. The medicinal drug transport mechanism for inflation of the balloon shaped member 22 is carried out by actuation and displacement of the plunger 28 of the syringe 14 in the longitudinal direction 12 to transport the medicinal drug 31 within the syringe chamber 30 through the flow channel 44, the opening (or slot) 54 into the interior 52 of the balloon shaped member 22. The balloon shaped member 22 subsequently assumes a somewhat ellipsoidal/spheroidal contour, as is seen in FIGS. 2 and 7, as was previously described.

The needle member 20 is then withdrawn from the interior 26 of the eye 40 while the balloon shaped member 22 remains within the patient's eye 40.

The balloon shaped member 22 may be maintained within the interior 26 of the eye 40 by the sutures 80 which are attached to the balloon proximal neck section 72 and extend through the sclera 24, as is seen in FIG. 6. In this manner, the balloon shaped member 22 is maintained at a relatively stable position within the interior 26 of the eye 40. In other embodiments, the balloon shaped member 22 may be left in a somewhat free-floating manner within the vitreous cavity thus negating the use of any fixing mechanisms for the balloon 22 within the eye 40.

Referring now to FIGS. 8A-8B and 10-12, there is shown an alternative embodiment 98 of the subject implant system 10 specified and described in FIGS. 1-7. The implant system 98 may include a pneumatic drive system 122, a syringe 100, a needle-shaped member (also referred to herein intermittently as an injection tube or a tubularly shaped injection member) 102, and a balloon 116.

Figure 10:
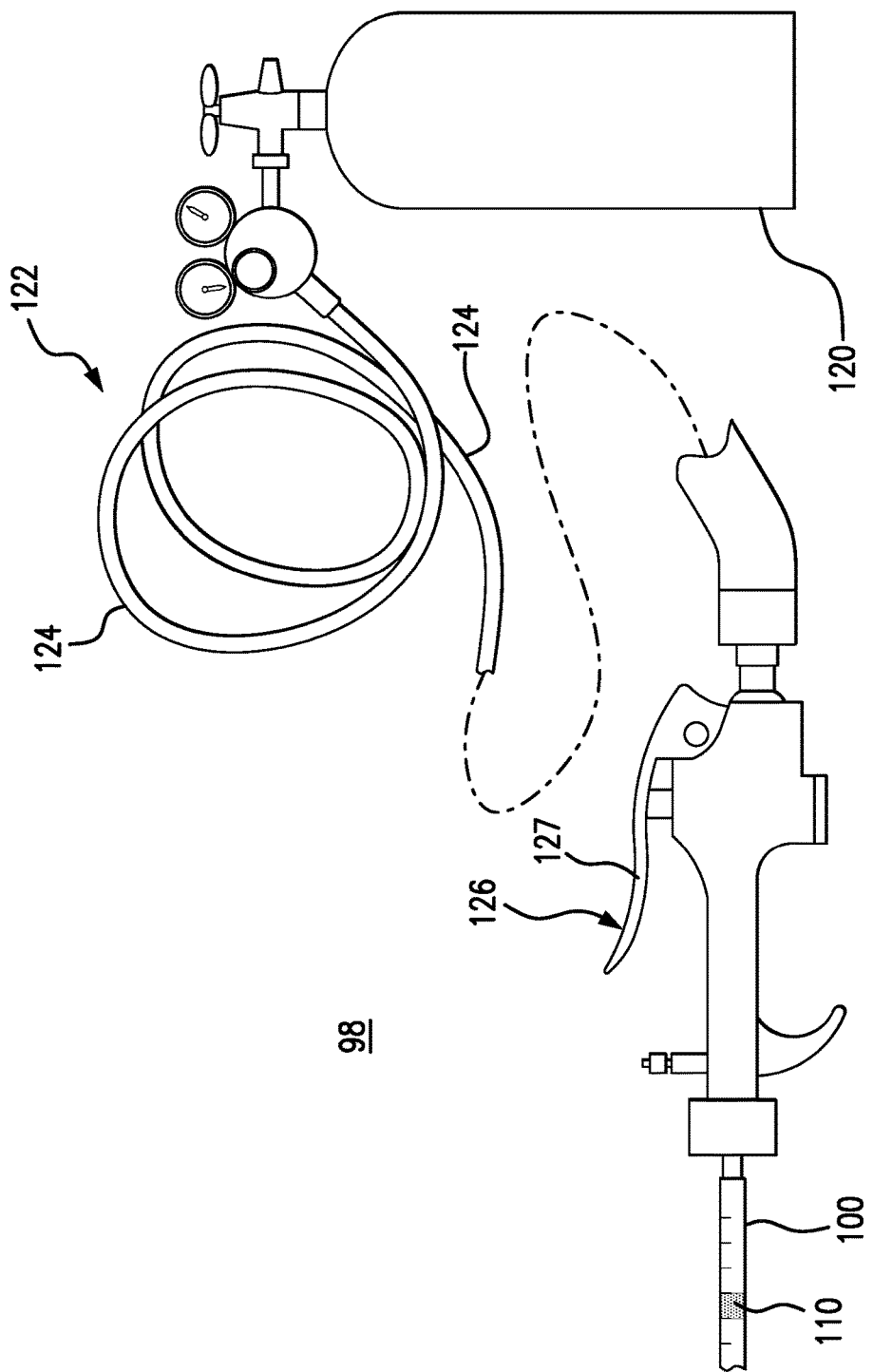
FIG. 10 is a schematic view of the embodiment of the subject implant system showing the pneumatic drive system.

As shown in FIG. 10, the pneumatic drive system 122 is coupled for fluid communication of high pressure air or other gaseous mixture into the syringe 100. By use of the pneumatic drive system 122, the medicinal drug 114 may be selectively controlled to provide passage of the medicinal drug 114 from the syringe 100 into the balloon 116.

Figure 8A:
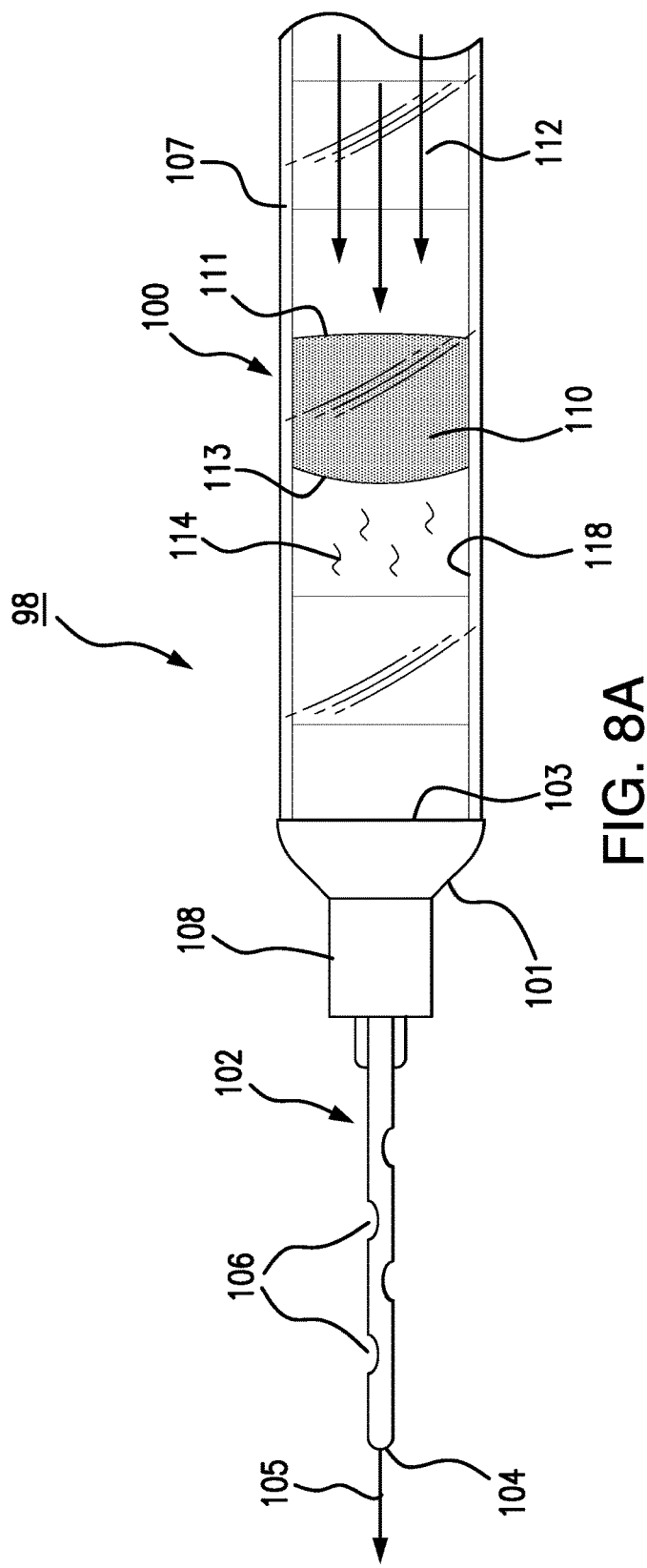
FIG. 8A is a schematic representation of an embodiment of the subject implant system showing a blunt needle (injection tube)

As seen in FIG. 8A, the syringe 100 has mounted therein a syringe plunger 110 which is slidably displaceable with respect to the syringe wall 107. In this manner, when the pneumatic drive system 122 is actuated, relatively high pressure air may be forced against the syringe plunger end section 111 when impinged by air flow from the pneumatic drive system 122 providing air flow in air flow direction 112.

Responsive to high pressure of the air impinging upon the plunger end surface 111, the syringe plunger 110 is displaced in a longitudinal direction with respect to the longitudinal axis 105 resulting in the displacement of the syringe plunger distal surface 113 in the direction of the longitudinal axis 105. In this manner, the medicinal drug 114 is transmitted from the syringe chamber 118 through an internal passage of the needle-shaped member 102 and transported through the needle ports 106 to the interior of the balloon 116.

The pneumatic drive system 122 includes a high pressure gas container 120 which is fluidly connected to a pneumatic actuator 126 having a pneumatic actuator handle 127 which may be manually controlled for passage of high pressure air therethrough. The pneumatic drive system 122 further includes pneumatic drive system tubular members 124 which are fluidly connected to both the pneumatic actuator 126 and the high pressure container 120, as is seen in FIG. 10.

In this manner, by manipulation of the pneumatic actuator handle 126, a controlled amount of high pressure air can pass through the pneumatic actuator 126 from the high pressure container 120 into the needle-shaped injection member 102 to provide a high pressure interface and force applied to the syringe plunger 110 which is then displaced in the direction of the longitudinal axis 105 to pass the medicinal drug 114 into the needle member 102 and then through the needle's injection ports 106. In this manner, the syringe 100 is adapted for selectively inserting and controlling a controlled dosage of the medicinal drug 114 into the interior of the balloon 116.

As shown in FIGS. 8A-8B, and 11-12, the syringe 100 is adapted to contain a medicinal drug 114 within a syringe chamber 118. Initially, a dosage of medicinal drug 114 is inserted into the syringe chamber 118 for further insert into the balloon 116, as will be described in following paragraphs.

The syringe 100 may be formed of a plastic-like composition, not important to the inventive concept as herein described, with the exception that it be structurally acceptable to the forces applied thereto. The syringe 100 includes a syringe cap 101 for closure of a distal syringe end 103 for maintenance of the medicinal drug 114 within syringe chamber 118 in a closed manner. In this manner, the dosage of medicinal drug 114 may be transported through the needle 102 and exit the tubularly shaped injection member 102 through the injection ports 106 for ultimate insertion into the interior of the balloon 116. The syringe cap 101 may include the syringe neck 108, as seen in FIG. 8A.

Figure 8B:
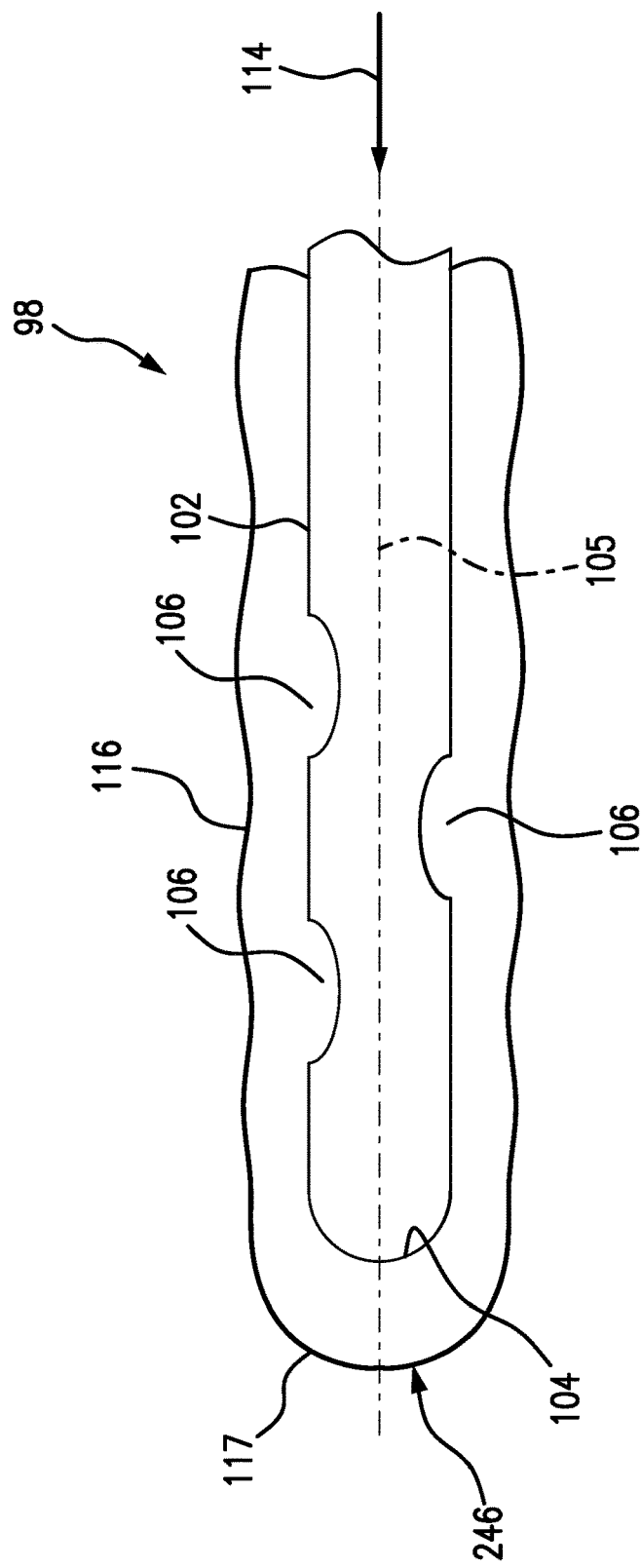
FIG. 8B is a schematic representation of the subject implant system showing the collapsed balloon member disposed over the blunt (closed) tip of the needle.

Referring to FIG. 8B, there is shown the embodiment implant system 98 where the tubularly shaped injection member (also referred to herein as the needle-shaped member, or needle) 102 includes a closed end (or blunt end) 104 wherein the balloon 116 is snugly mounted on and envelopes the blunt end 104 of the needle 102. In this embodiment, the balloon's distal end 246 is closed.

Figure 9:
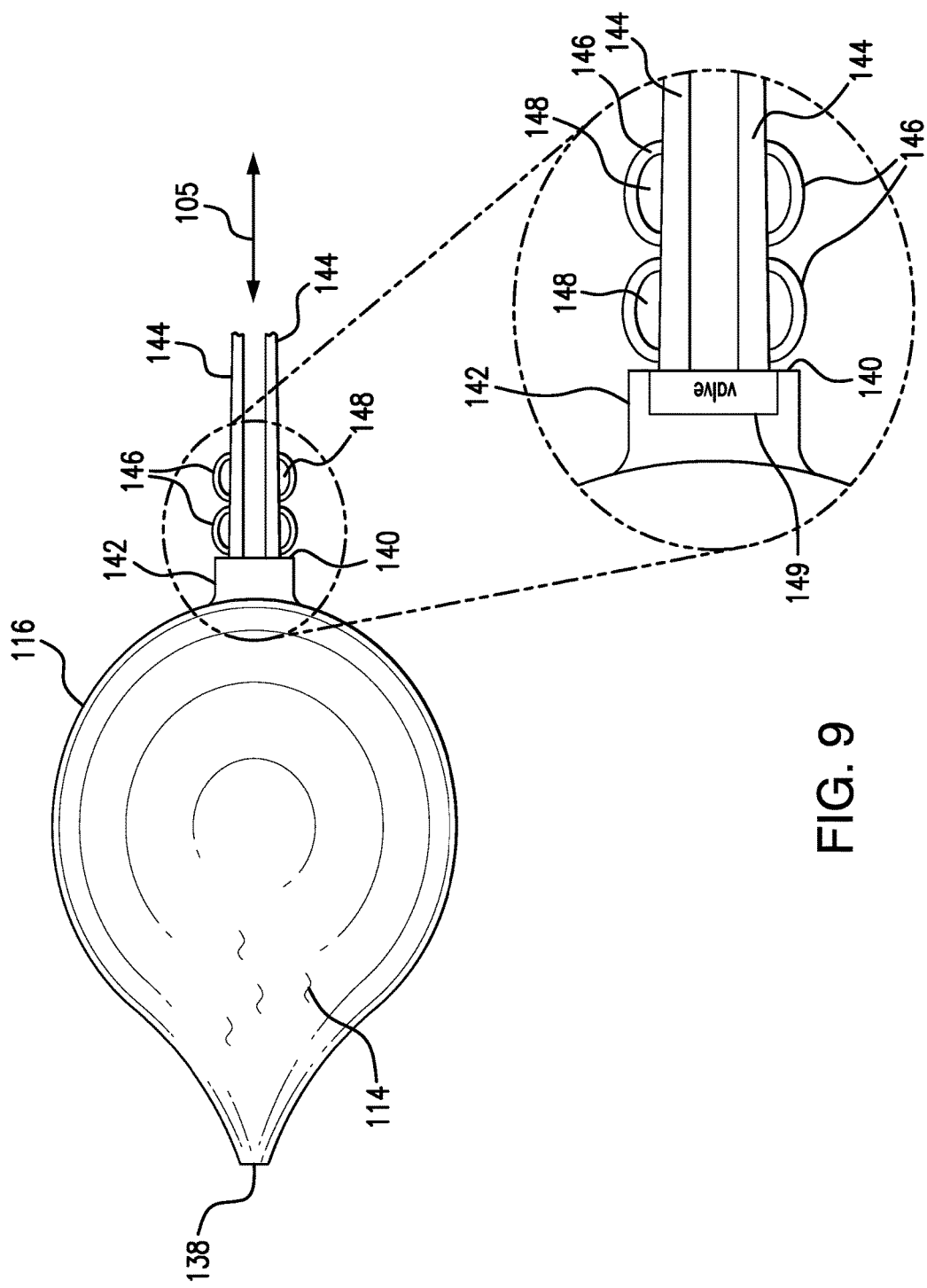
FIG. 9 is a blow-out portion of the subject implant embodiment showing the balloon shaped member and a suture section for attachment to the patient's eye.

In operation, the medicinal drug 114 passes through the interior passage of the needle-shaped member 102 and is expelled through the side injection ports 106 formed in the sidewalls of needle 102. Side injection ports 106 are formed through a wall of the needle-shaped member 102 around the circumferential surface of the needle-shaped member 102 and are in fluid communication with the interior passage of the needle-shaped member 102 to permit the medicinal drug 114 to be transported to the interior of the balloon 116, as shown in FIG. 9.

In the embodiment of the invention concept shown in FIGS. 8A-8B and 11-12, the needle-shaped member 102 has a closed needle distal end 104. Essentially, this provides for a closed (blunt) edge distal end 104 for the needle-shaped member 102 to permit the medicinal drug 114 to pass into the balloon 116 only through the side injection ports 106.

The needle-shaped member 102 may be formed as an tubularly shaped injection member of a metal composition, such as stainless steel or some like metallic composition which is non-reactive with respect to the medicinal drug 114 being inserted into the balloon 116.

The injection ports 106 may be formed on opposing sides of the needle-shaped member 102 or in some other generally symmetric arrangement around the crossing periphery of the needle-shaped member 102. There are generally a plurality of the injection ports 106 formed through the sidewall of the needle-shaped member 102 and arranged around the longitudinal axis 105.

Figure 11:
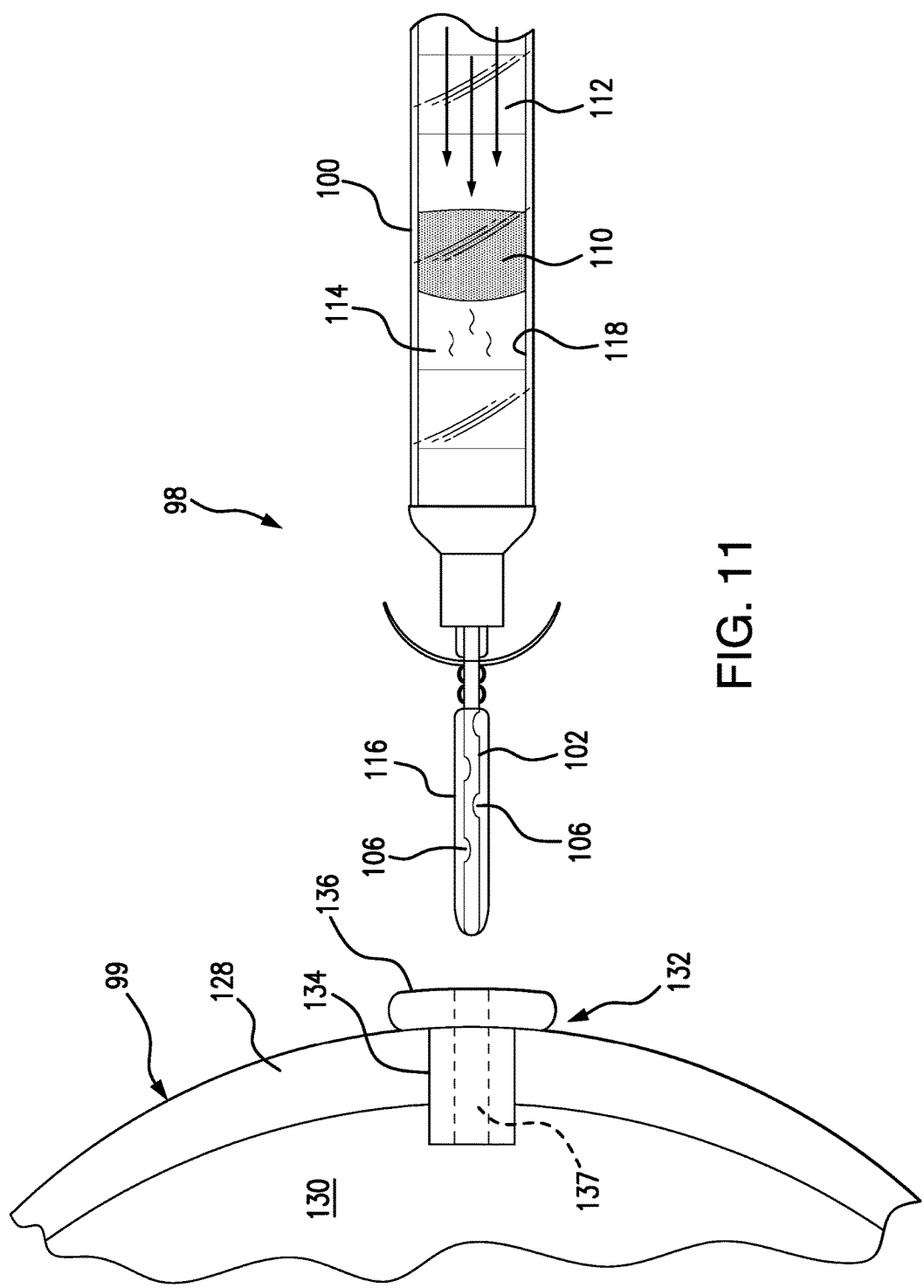
FIG. 11 is a schematic view of the subject implant system embodiment showing the locational positioning prior to insertion of the deflated balloon shaped member through a canula.

Referring now to FIG. 11, prior to insertion of the needle-shaped member 102 into the interior portion 130 of the eye 99 of the patient, a cannula 132 is preferably inserted through the sclera 128. The cannula 132 is formed of a bio-compatible composition which may be an inert plastic composition or other type of composition acceptable for insertion into the interior 130 of the eye 99. The cannula 132 includes a cannula neck section 134 as well as a cannula head section 136. The extension of cannula neck section 134 must be of a sufficient length to at least protrude slightly into the interior portion 130 of the eye 99 through the sclera 128. The cannula head section 136 has a diameter greater than the diameter of the cannula neck section 134 and is positioned adjacent an exterior surface of the eye 99. In this manner, cannula 132 is positioned and mounted on the external surface of the sclera 128, as shown in FIG. 11.

As seen in FIG. 11, prior to expansion of the balloon 116, the unexpanded balloon 116 is mounted on the needle-shaped member 102 for subsequent passage through the cannula 132 through the opened internal channel 137. In FIG. 11, the balloon 116 is shown in its unexpanded (deflated, or collapsed) state and has been prepared for insertion through the opened internal channel 137 of the cannula 132 to the interior section 130 of the eye 99.

Subsequent to insertion of the needle-shaped member 102 into the interior 130 of the eye 99, the balloon 116 is expanded (as is shown in FIG. 9), responsive to the displacement of the plunger 110 forcing or transmitting the medicinal drug 114 through the interior passage along the tubularly shaped injection member 102 and the side injection ports 106 into the interior of the balloon 116.

Referring to FIG. 9, there is shown the balloon member 116 in an expanded state with associated elements to be described. The balloon 116 includes a balloon distal end section 138 and a balloon proximal end 140. The expanded state of the balloon 116 shown in FIG. 9 is a contour which is achieved subsequent to insertion of the medicinal drug 114 into the interior of the balloon 116. As was the case for the balloon shaped member 22 depicted in FIGS. 1-7, the balloon shaped member 116 is formed of a bioresorbable composition, which degrades in the patient's body and thus does not necessitate removal from the therapeutical site after the medicinal agent has been dispensed therefrom.

The proximal end 140 of the balloon shaped member 116 includes a neck portion 142 extending from a surface of the balloon shaped member 116. Prong members 144 extend in the direction 105 from the balloon neck 142 and are generally formed in one-piece formation with the balloon neck 142 and the balloon shaped member 116. The prong members 144 extending from the balloon shaped member 116 may be formed of an elastically deformable composition, such as a plastic composition, or some other elastically deformable composition which is bio-compatible with the patient's tissue.

The prong members 144 are elastically deformable during the ophthalmic procedure of the insertion of the balloon shaped member 116 into the interior 130 of the patient's eye 99.

Mounted on the prongs 144 are suture fixation elements 146 formed on the prongs 144 to permit suturing of the balloon shaped member 116 to the patient's eye 99. The suture fixture elements 146 are formed on the prong members 144 in a "loop" manner and are formed integral with the balloon prong members 144 to provide suture fixation element openings 148 through which sutures may be passed.

In overall concept, the balloon neck 142 provides for anchor struts for anchoring the balloon implant 116 to the sclera or eye wall. The balloon neck 142 may be laser cut into semi-circular elements 146 defining the suture fixation elements which are then used for passing of the fixation sutures therethrough.

The balloon distal end 138 is closed and thus, any medicinal drug 114 is transmitted through the proximal balloon end 140. The proximal balloon end 140 may be closed with a member 149, such as a permeable membrane, a flap valve, or other type check valve, schematically depicted in FIG. 9. In this manner, the medicinal drug 114 is passed from the interior of the balloon shaped member 116 through the balloon membrane into the interior portion 130 of the patient's eye 99.

Figure 12:
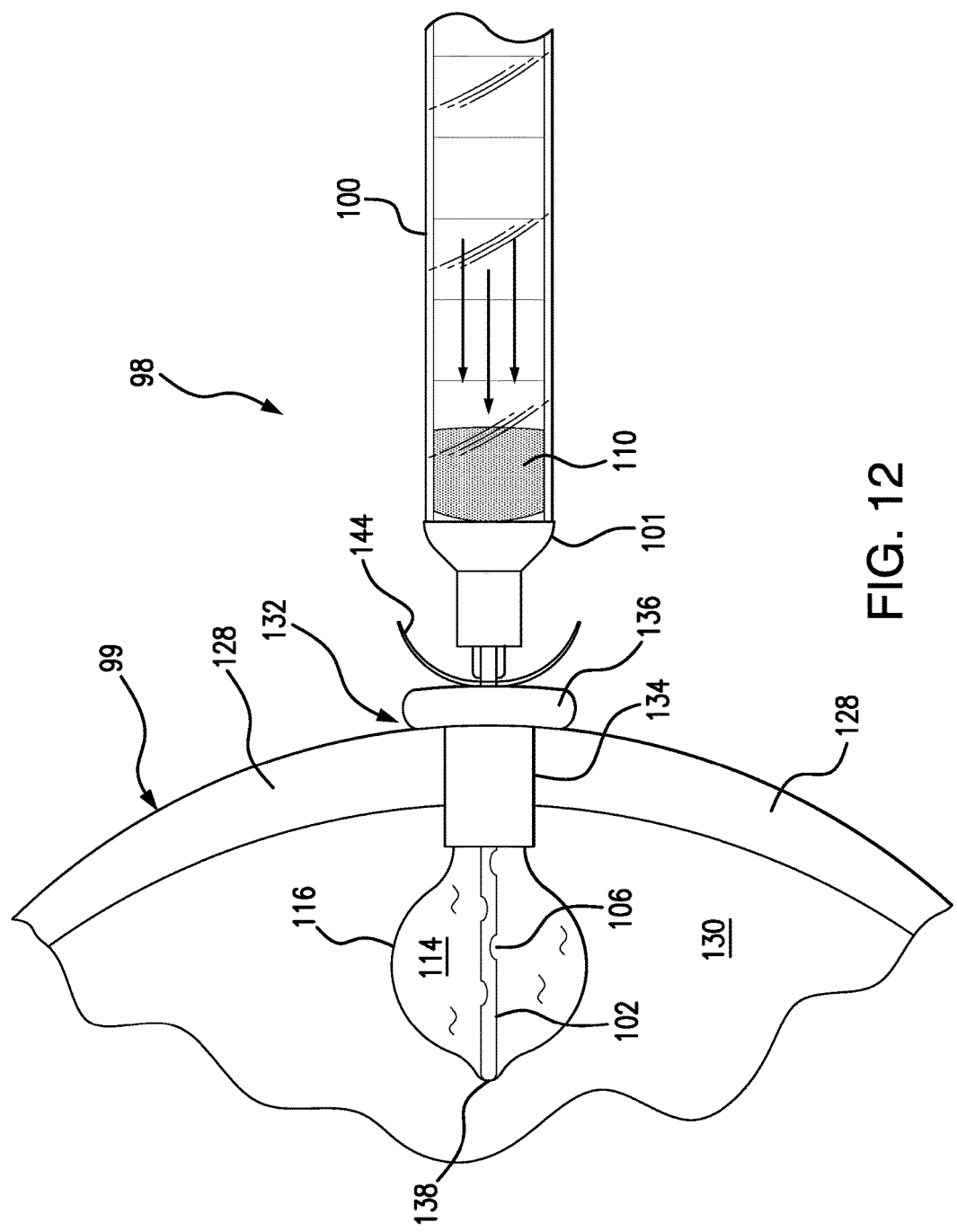
FIG. 12 is a schematic view of the subject implant system embodiment with the balloon shaped member inflated within the eye of the patient.

Referring now to FIG. 12, during the procedure, the cannula 132 has been inserted through the sclera 128 with the needle 102 being positioned internal to the interior portion 130 of the patient's eye 99. In the depiction shown in FIG. 12, the needle-shaped member 102 has passed into the eye 99, and the balloon shaped member 116 is shown as being inflated. In this position, the needle-shaped member 102 has passed through the cannula 132 through the opening (internal channel) 137 and is mounted in a manner where the suture fixation elements 146 are at least partially within the sclera 128, as is depicted in FIG. 13. Once the balloon shaped member 116 is positioned within the interior portion 130 of the patient's eye 99, release of the medicinal fluid 114 is provided through the balloon neck 142.

Referring now to the subject procedure of the balloon implanting insertion and balloon inflation within the interior portion 130 of the eye 99, the balloon shaped member 116, as shown in FIG. 11 in its unexpanded state, is mounted over the needle-shaped member 102. The needle-shaped member 102 is then transported through the cannula 132, specifically, through the opening 137, into the interior portion 130 of the patient's eye 99.

The pneumatic actuator 126 (shown in FIG. 10) is then actuated to provide high pressure air or other gaseous media against the plunger end surface 111 to drive the medicinal drug 114 through the interior of the needle 102 and through the ports 106 to the interior of the balloon 116 to provide inflation of the balloon 116 within internally of the eye 99.

In this placement, as seen in FIG. 13, the suture fixture elements 146 are at least partially located within the sclera 128.

Once the balloon 116 has been inflated (subsequent to positioning within the patient's body), the needle-shaped member 102 is retracted through the cannula neck section 134 with the suture fixation elements 146 being at least partially internal to the sclera 128. Once the balloon 116 has been inflated, the needle member 102 is retracted through the cannula neck section 134 and the cannula 132 is removed from the sclera 128 with the suture fixation elements 146 remaining at least partially within the sclera 128, as has previously been described for FIG. 13.

Referring now to FIGS. 13 and 14, subsequent to the cannula 132 being removed from the sclera 128, the prong elements 144 may be either cut or trimmed. The suture fixture elements 146 may remain at least partially within the sclera 128. Once the needle 102 has been removed, the sutures 150 are passed through openings 148 in the suture fixture elements 146 to provide a fixing of the balloon 116 within the interior portion 130 of the patient's eye 99.

The balloon distal end 138 is closed and is formed of a non-permeable composition and does not permit passage of the medicinal drug 114 external to the balloon 116. The balloon proximal end 140 may be formed with a permeable membrane 145 to permit medicinal drug 114 to pass therethrough to the interior 130 of the eye 99. In an alternative embodiment, the balloon proximal end 140 may have a check valve 149 (schematically depicted in FIG. 9) such as, for example, a flap valve, which is permeable to medicinal drug 114 to permit egress of medicinal drug 114 external to the balloon 116 and passage of the medicinal drug 114 into the interior 130 of the patient's eye 99 in a controlled manner.

Referring to FIGS. 15-22, another alternative implant embodiment 200 of the subject system 10 is presented.

Referring to FIGS. 15 and 16A-16B, the balloon member (also referred to herein as a balloon, a balloon-shaped member, or balloon implant) 202 is shown in a collapsed (deflated) state. The balloon member 202 includes a balloon distal end section 204 and a balloon proximal section 206. The proximal section 206 of the balloon member 202 includes a neck portion 208 extending from the surface of the balloon member 202. Similarly, the distal section 204 of the balloon 202 includes a neck portion 210. The neck portion 210, at the proximal end 206 of the balloon 202, similar to the neck 208, extends from the surface of the balloon member 202.

As shown in FIGS. 15 and 16A-16B, the neck 208 of the balloon 202 of FIG. 15 has been modified to form prong members 212 extending in the direction 105 from the balloon's proximal neck 208 at the proximal end 206 thereof. The prong members 212 are preferably formed by laser cut technology in integral formation with the balloon neck 208 of the balloon shaped member 202. The prong members 212 extend from the balloon member 202 and are formed of an elastically deformable bio-resorbable composition, such as a plastic composition or some other elastically deformable composition which is bio-compatible with a patient's tissue, and preferably, from the same material as the material of the balloon 202. The prong members 212 are elastically deformable during the procedure of the implantation of the balloon shaped member 202 into the interior of the patient's eye, thus facilitating the implantation procedure.

Mounted on the prongs 212, are suture fixation elements 214 formed on the prongs 144 (preferably by laser cut technology) to permit suturing of the balloon shaped member 202 to the patient's eye. The suture fixture elements 214 are formed on the prong members 212 in a "loop" manner and are formed integral with the balloon prong members 212 to provide suture fixation element openings 216 through which sutures may be passed by a surgeon. The balloon neck 208 on the proximal section 206 of the balloon shaped member 202 provides for anchor struts to anchor the balloon implant 202 to the sclera or eye wall, or at any sub-cutaneous site on the patient's body.

Shown in FIGS. 17A-17B is a laser cut plug 220 which may be formed from the same (or other) bio-resorbable material used for the balloon shaped member 202. The plug 220 has a profile which is created with laser cut technology and has a sealed end 222 and an opposite end 224 which is shaped with two leg members 228 extending in a somewhat spaced apart relationship each from the other (as shown in the side view of the plug 220 in FIG. 17A). The leg members 228 are capable of being resiliently brought in contact to each other for being inserted into the injection tube 230 as shown in FIGS. 18-19.

The injection tube 230 (depicted in FIG. 18), also referred to herein as the tubularly shaped injection member, is similar to the needle 102 shown in FIGS. 8A-8B and 11-12, and has a distal end 232 and a proximal end 234.

Figure 19:
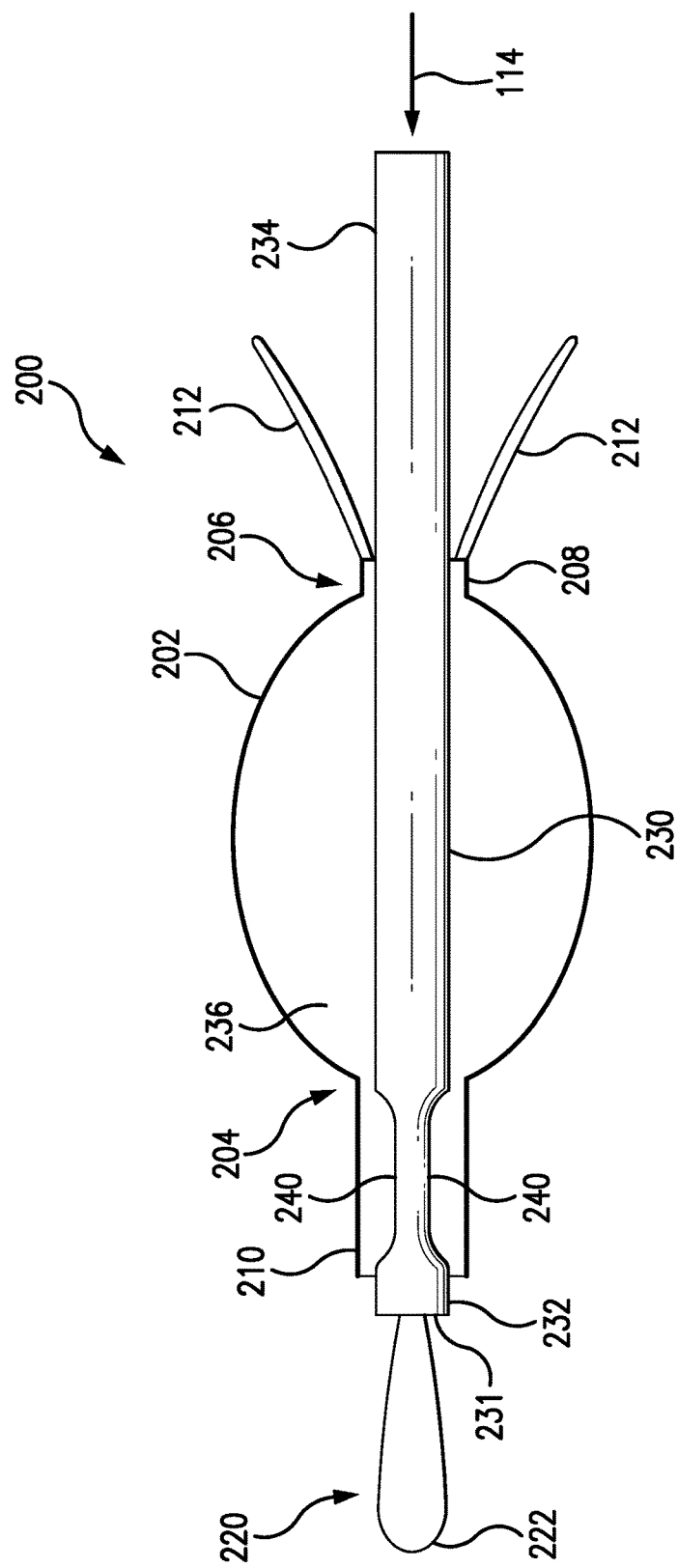
FIG. 19 shows schematically the assembled subject implant system in its alternative embodiment prior to insertion of the balloon implant into the patient's body (depicting the injection tube inserted in the balloon shaped member, and the laser cut plug attached at the distal end of the injection tube)

As shown in FIG. 19, initially the injection tube 230 may be inserted into the balloon shaped member 202 with the distal end 232 of the injection tube 230 extending outside the neck 210 at the distal section 204 of the balloon 202.

The plug 220 is attached to the distal end 232 of the injection tube 230. In order to attach the plug 220 into the distal end 232 of the injection tube 230, the leg members 228 of the plug 220 are resiliently brought together and inserted into the port (opening) 231 formed at the distal end 232 of the injection tube 230. The sealed end 222 of the plug 220 extends outside the distal end 232 of the injection tube 230. The attached plug 220 thus seals (closes) the distal end 232 of the injection tube 230. The injection tube 230 has injection ports 240 formed in proximity to its distal end 232.

Figure 20:
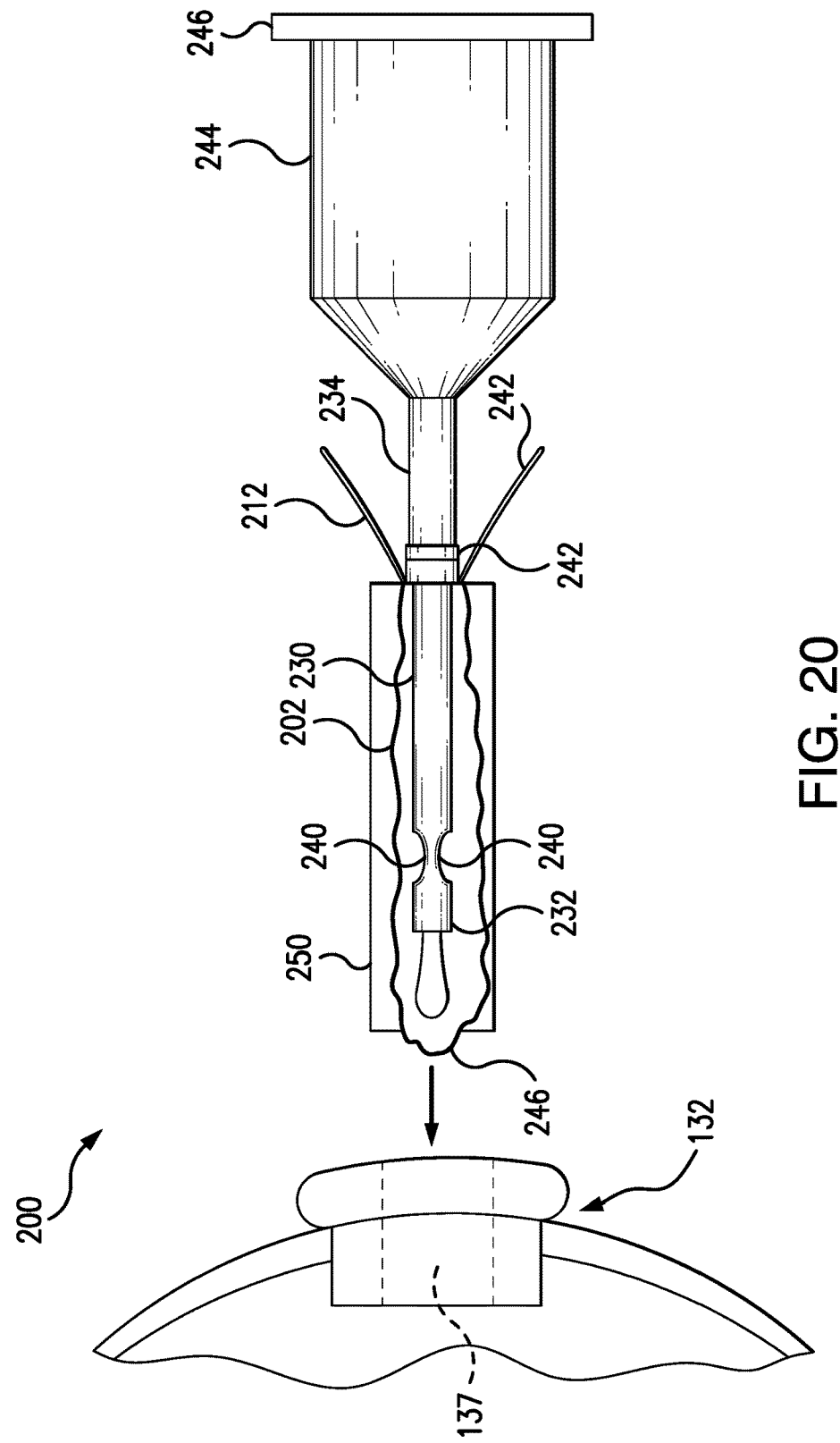
FIG. 20 is a schematic view of the subject implant system (in an alternative embodiment) depicting the locational positioning prior to insertion of the collapsed balloon through a canula.
Figure 21:
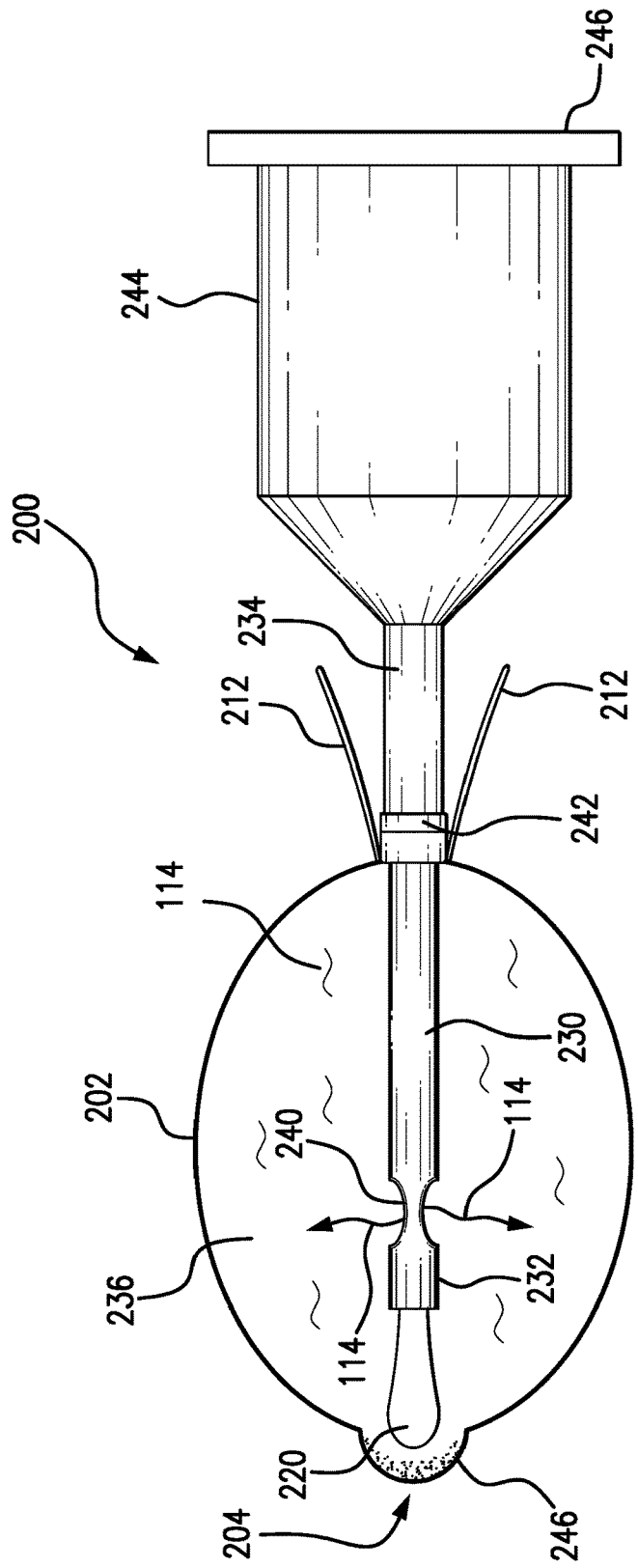
FIG. 21 is a schematic representation of the system (in an alternative embodiment) where the injection tube is attached to the hub of the syringe, and retracted into the balloon having a sealed off distal end (with the injection port inside of the balloon and the injection tube stop member attached to the injection tube member to prevent undesirable insertion of the injection tube all the way into the balloon shaped member)

Referring to FIGS. 20-21, the injection tube 230 is subsequently displaced into the interior 236 of the balloon 202.

Figure 22:
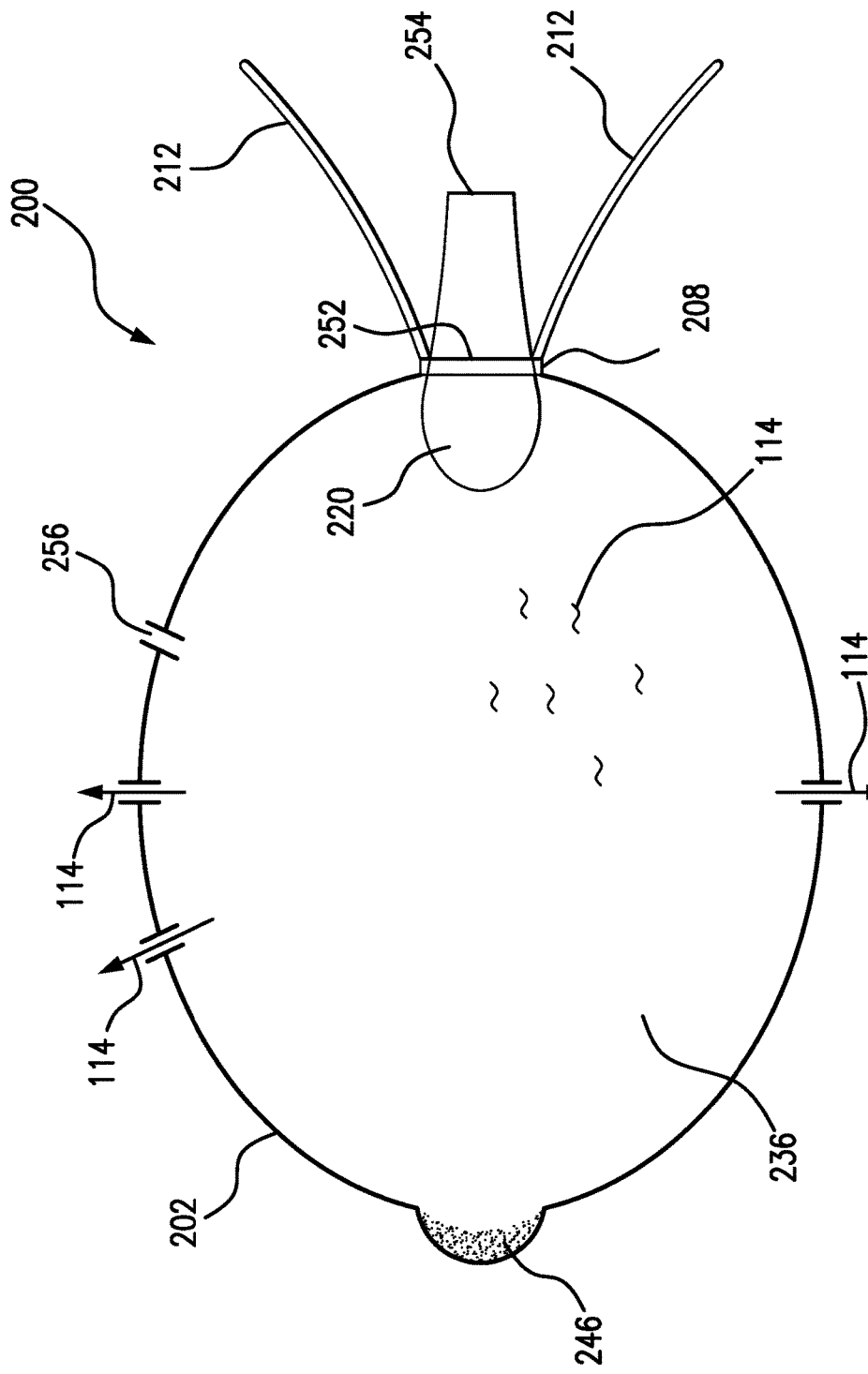
FIG. 22 shows the inflated balloon implant with the self-deploying plug wedged in its proximal section neck as the result of the injection tube (needle) retraction from the balloon.

Referring to FIGS. 20-22, the front end 246 at the distal section of the balloon 202 is sealed off. A tube stop 242 is inserted at the proximal end 234 of the injection tube 230. The proximal end 234 of the injection tube 230 is attached to the hub member 244 of the syringe 246.

The tube stop 242 provided at the predetermined location of the injection tube 230, prevents the insertion of the injection tube 230 into the balloon 202 further than desired. Specifically, the tube stop member 242 prevents the distal end 232 of the injection tube 230 to extend through the sealed-off end 246 at the distal section 204 of the balloon member 202.

Referring again to FIG. 20, a containment sleeve 250 may be slid over the collapsed balloon 202 (while the collapsed balloon 202 envelops the injection tube 230 along with plug 220 attached to its distal end 232). The deflated balloon 202 contained within the containment sleeve 250 may be inserted into the patient's body specifically through the sclera 128 to the interior of the patient's eye, or any other space within the patient's body. During the insertion procedure, the containment sleeve 250 is inserted into the sclera, preferably through the (opening) passage 137 formed in the cannula 132 (as also shown in FIGS. 11 and 12), and, when in place, the containment sleeve 250 is retracted from the patient's body.

The self-deploying valve 220 is attached to the distal end 32 of the injection tube (injection needle) 230 that resides in the inside of the collapsed balloon 202 until such time that the balloon implant 202 is inflated with the medicinal agent 114.

Subsequently, as shown in FIG. 21, the medicinal agent 114 is injected into the balloon 202 via the injection ports 240 formed at the injection tube 230. The inflated balloon 202 filled with the medicinal agent 114 subsequently assumes the shape shown in FIGS. 21-22.

After the balloon 202 is inflated with the medicinal agent 114, the injection needle (injection tube) 230 is withdrawn from the balloon implant 202 and the patient's body.

Subsequent to injection, the injection tube 230 is retracted from the patient's eye (or any other organ of the body). When the insertion tube 230 is withdrawn from the patient's body, the plug 220 closing the distal end 232 of the injection tube 230, is also moved out (by the motion of the insertion tube 230) in the direction coinciding with the direction of the injection tube motion. When the plug 220 reaches the proximal neck 208 of the balloon 202, as shown in FIG. 22, it wedges itself into the opening 252 of the neck 208, thereby effectively sealing the proximal end 204 of the balloon implant 202.

The plug 220 constitutes a self-deploying valve that is designed to prevent the collapse of the balloon implant 202 or loss of the medicinal agent 114 from the interior 236 of the balloon 202. The self-deploying valve (plug) 220 occludes the balloon's proximal neck 208, thus preventing leakage of the medicinal fluid from the balloon implant 202 therethrough.

The leg members 228 at the end 226 of the plug 220 that are attached to the injection tube 230 either tear away from the wedged valve 220 by their perforation 254 shown in FIGS. 17A, 17B, or are cut away by a surgeon.

The balloon's distal end 204, and specifically the front end 246 of the balloon 202, is closed (sealed off) and is formed of a non-permeable composition, and thus does not permit passage of the medicinal drug 114 external to the balloon 202.

When the balloon proximal end 206 is equipped with the plug 220 (which occludes the passage of the medicinal drug through the opening 252 in the proximal end 206 of the balloon 202), and the front end 246 of the balloon 202 is sealed off, the egress of the medicinal drug 114 external to the balloon 202 and passage of the medicinal drug 114 into the interior of the patient's eye may be through the pores 256 formed in the walls of the balloon member 202 which in this embodiment is formed from a porous material.

Subsequently to retraction of the containment sleeve 250 and the injection tube 230 from the patient's body, the prong elements 212 (or the balloon 202) may be either cut or trimmed. The suture fixture elements 214 remain at least partially within the patient body. Once the injection tube 230 has been removed, the sutures may be passed through the openings 216 and the suture fixture elements 214 to provide a fixing of the balloon 202 within the interior of the patient's eye.

Figure 23:
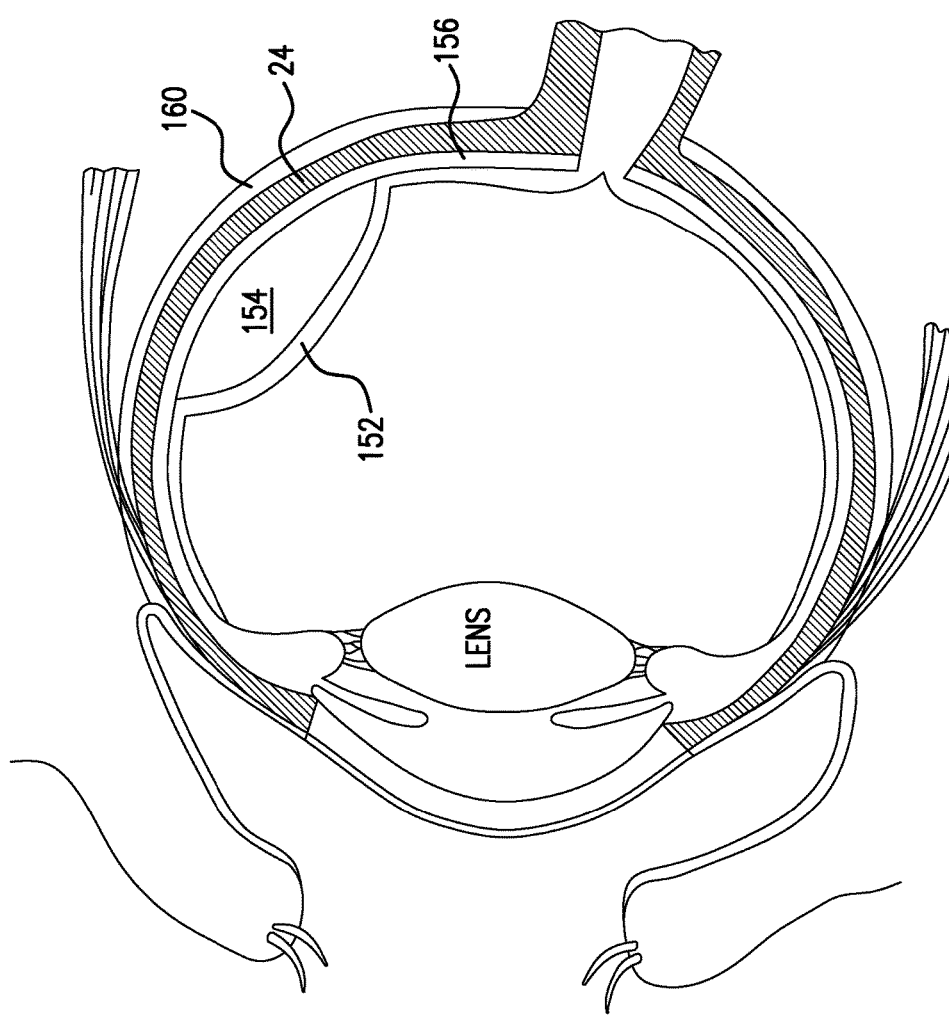
FIG. 23 is a schematic view showing in cross-section a detached retina of a patient's eye.
Figure 24A:
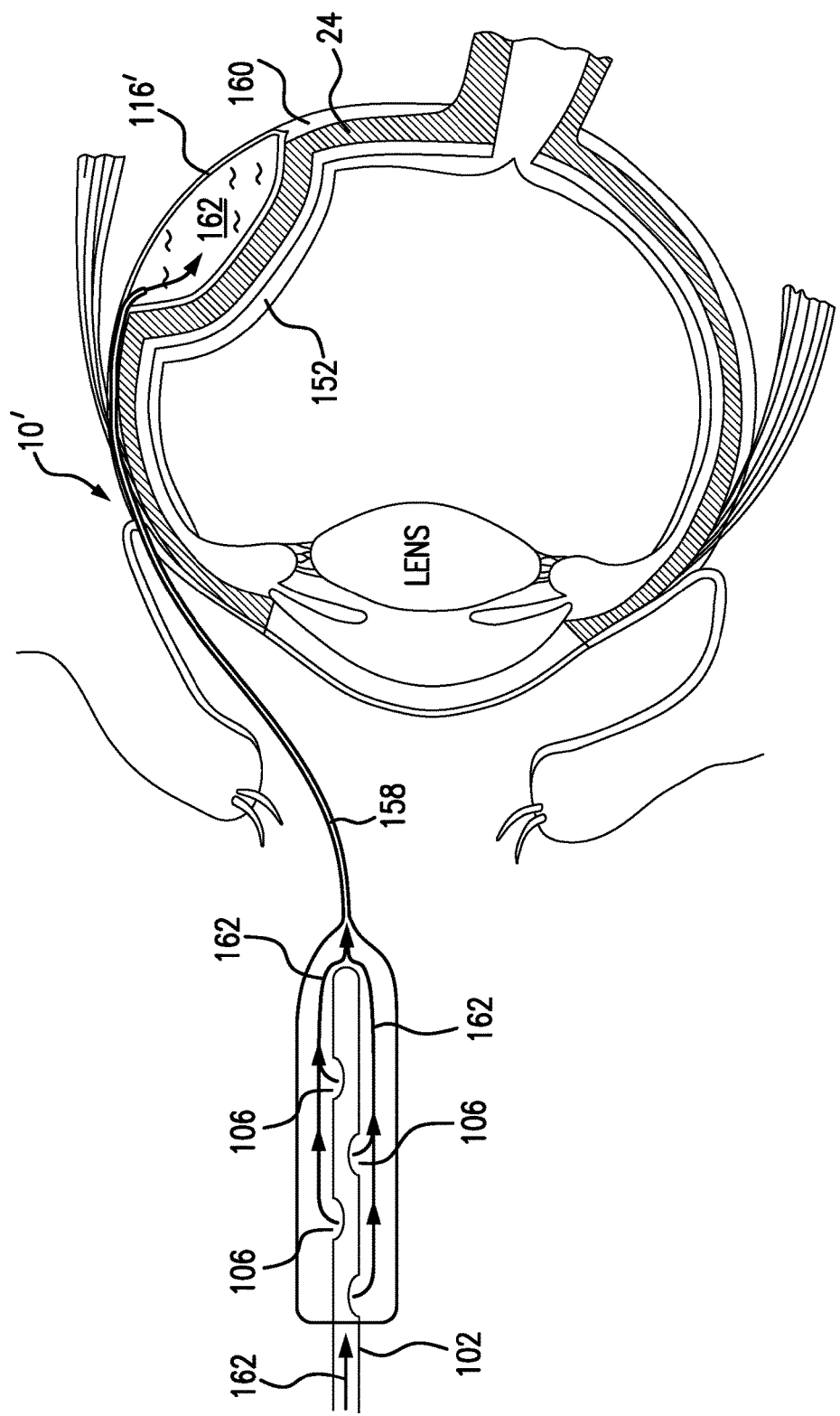
FIGS. 24A-24B are schematic views showing in cross-section a further embodiment of the subject implant system where a working fluid is inserted into the balloon shaped member for reattaching a patient's retina to the sclera, via a flexible tubing (FIG. 24A) or rigid tubing (FIG. 24B) in direct fluid connection with the balloon shaped member.
Figure 24B:
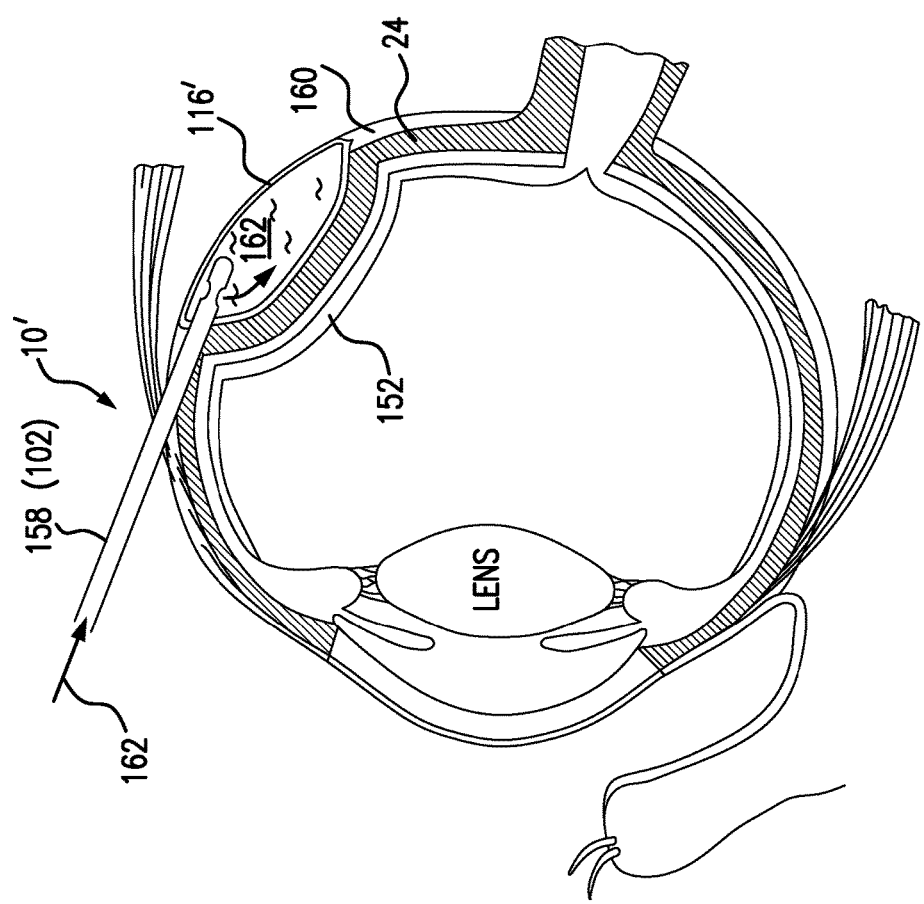

Referring now to FIGS. 23 and 24A-24B, there is shown an embodiment of implant system 10 which provides for reattachment of a detached retina. As seen in FIG. 23, the retina 152 is detached from the sclera 24, thus forming a detached region 154 between the retina 152 and the choroid 156. Detachment of the retina 152 from the choroid 156 is an emergency situation, and needs to be ophthalmologically treated on an expedited basis. It may provide a variety of symptoms such as the appearance of floaters which are tiny specks, may drift through the field of vision, possibly flashes of light, blurred vision, a gradual reducing of peripheral vision, or a shadow formed over a visual field of view, and may result in loss of vision, if left untreated.

In order to re-attach the sclera 24 to the retina 152, an embodiment of the subject implant system 10' is shown in FIGS. 24A-24B. In this embodiment, the implant system 10' may be provided with the same or similar syringe 100 actuated by a pneumatic drive system 122, as provided in FIG. 10, or may be manually actuated to drive the syringe plunger 110 through a predetermined distance within the syringe 100 to eject or emit a working fluid 162.

In this embodiment, as seen in FIG. 24A, a needle similar to needle 102 is coupled in fluid communication with a tubing 158. In one embodiment, the tubing 158 may be a flexible tubing, as shown in FIG. 24A. The needle 102 may include the side ports 106 described in other embodiments of the subject implant system, or in the alternative, may have a through opening for releasable attachment to the flexible tubing 158. The flexible tubing 158 is then coupled to the balloon 116', and the flexible tubing 158 along with the balloon 116' are then inserted into the Tenon space 160 of the eye. Once inserted into the area which is adjacent to the detached region 154 (shown in FIG. 23), the balloon 116' is inflated, as shown in FIG. 24A, where the interior of balloon 116' is filled with a working fluid 162. The inflated balloon 116' creates a force which is applied against the sclera 24 to displace the sclera 24 against the retina 152. In this manner, the sclera 24 is joined to the retina 152 to keep the retina and the sclera in contiguous contact for a predetermined time duration sufficient for the healing process to permit reattachment of the retina to the sclera.

In another embodiment, shown in FIG. 24B, the tubing 158 may be a rigid needle, similar, for example, to the needle 102, which is inserted into the eye and serves for inflating the balloon 116'.

Subsequent to re-attachment of the retina 152 to the sclera 24, after some predetermined time interval, the flexible or rigid tubing 158 may be removed from the balloon 116', and withdrawn from the Tenon space 160.

Once the tubing 158 has been removed from the Tenon space 160, the working fluid contained within the balloon 116' is maintained in relatively fixed orientation in order to allow healing of the sclera 24 in fixed relation to the retina 152.

The balloon 116' may include a check valve to maintain the working fluid within balloon 116' in order to allow the healing to take place.

Subsequent to the healing process, a further probe may be inserted into balloon 116' in the manner of flexible or rigid tubing 158 to allow removal of the working fluid and subsequent removal of the balloon 116' (if balloon 116' is not formed of a bio-resorbable composition), with the retina 152 being reattached to the sclera 24.

In preferred embodiments of the procedure, as shown in FIGS. 24A-24B, the balloon 116' may be bio-resorbable and permit a "dissolution" of the balloon 116' in the patient's eye, thus resulting in a "natural removal" of the balloon 116' from the region 154 through the bio-resorption of the balloon's wall membranes to provide a gradual healing process where the retina 152 is reattached to the sclera 24 without an additional surgical removal of the balloon from the eye.

Although this invention has been described in connection with specific forms and embodiments thereof, it is to be appreciated that various modifications other than those discussed above may be resorted to without departing from the spirit or scope of the invention. For example, functionally equivalent elements may be substituted for those specifically shown and described, certain features may be used independently of other features, and in certain cases, particular locations of elements, steps, or processes, may be reversed or interposed, all without departing from the spirit of the invention as herein disclosed.

What is claimed is:

1. A bioresorbable sub-cutaneous implant system comprising:
   a balloon member having a closed distal end and a proximal end and formed of a biodegradable composition, said balloon member being capable of transformation between an unexpanded configuration and an expanded configuration;
   a syringe equipped with a displaceable member disposed internally thereof and a tubularly shaped injection member attached to said syringe at one end thereof;
   a medical agent contained in an external chamber disposed in said syringe externally of a patient's body; and the tubularly shaped injection member releasably coupled to said balloon member for implanting said balloon member into the patient's body, and said displaceable member controllably displaceable in said syringe and operatively coupled to said medicinal agent contained in said external chamber, said displaceable member being actuatable for transporting said medicinal agent from said external chamber into an interior of said balloon member subsequent to implanting of said balloon member in the patient's body, said tubularly shaped injection member having a closed distal section, a central section and a proximal section, wherein said tubularly shaped injection member is configured with at least one injection opening formed through a wall of said central section of said tubularly shaped injection member and supporting a fluid communication between said interior of said balloon member and said external chamber;

wherein said balloon member has a closed distal end section enveloping said closed distal section of said tubularly shaped injection member, and a proximal end section releasably secured to said proximal section of said tubularly shaped injection member with the interior of said balloon member extending over said central section of said tubularly shaped injection member between said closed distal section and said proximal section thereof in alignment with said at least one injection opening for receiving therethrough said medicinal agent transported from said external chamber;

wherein said balloon member assumes said unexpanded configuration for being implanted in the patient's body by said tubularly shaped injection member, and said expanded configuration after implantation in the patient's body by said tubularly shaped injection member and upon a controllable actuation of said displaceable member to transport said medical agent from said external chamber into said interior of said balloon member through said at least one injection opening formed through the wall of said tubularly shaped injection member; and wherein said tubularly shaped injection member is fully removable from said interior of said balloon member after said interior of said balloon member is filled with said medicinal agent, and wherein said medicinal agent is released from the interior of said balloon member into the patient's body at least through the proximal end section of said balloon member.

2. The system of claim 1, wherein said displaceable member is a displaceable syringe plunger received internally of said syringe and controllably reciprocable therein along the longitudinal axis of said syringe.

3. The system of claim 1, where said at least one injection opening formed through the wall of said central section of said tubularly shaped injection member is placed in alignment with a central section of said balloon member for transport of said medicinal agent from said external chamber into said interior of said balloon member.

4. The system of claim 3, wherein said at least one injection opening includes a plurality of ports placed around the longitudinal axis of said tubularly shaped injection member.

5. The system of claim 1, wherein the syringe has a first end and a second end, said external chamber being positioned internally of said syringe between said first and second ends thereof,
 a sleeve member slidably positioned on said proximal section of said tubularly shaped injection member between said proximal end section of said balloon member and said syringe.

6. The system of claim 5, further including a fixing member secured to said proximal section of said tubularly shaped injection member for controlling a depth of said tubularly shaped injection member insertion within the body of the patient subsequent to insertion of said tubularly shaped injection member, and where an external diameter of said fixing member is greater than an outer diameter of said tubularly shaped injection member proximal section and less than an outer diameter of said sleeve member.

7. The system of claim 1, where said at least one injection opening formed through said wall of said central section of said tubularly shaped injection member forms an elongated slot contour through said central section of said tubularly shaped injection member.

8. The system as recited in claim 1, where said balloon member assumes at least a partial ellipsoidal or spheroidal contour subsequent to said medicinal agent transportation through said at least one injection opening formed through said wall of said central section of said tubularly shaped injection member.

9. The system of claim 1, further including a securing mechanism for fixing said balloon member within the body of the patient subsequent to said balloon member assuming said expanded configuration thereof.

* * * * *